(12) United States Patent
Hosokawa

(10) Patent No.: US 11,092,529 B2
(45) Date of Patent: Aug. 17, 2021

(54) BLOOD COAGULATION TEST DEVICE AND BLOOD COAGULATION TEST METHOD

(71) Applicant: FUJIMORI KOGYO CO., LTD., Tokyo (JP)

(72) Inventor: Kazuya Hosokawa, Tokyo (JP)

(73) Assignee: FUJIMORI KOGYO CO., LTD., Tokyo (JP)

( * ) Notice: Subject to any disclaimer, the term of this patent is extended or adjusted under 35 U.S.C. 154(b) by 137 days.

(21) Appl. No.: 16/329,243

(22) PCT Filed: Aug. 28, 2017

(86) PCT No.: PCT/JP2017/030773
§ 371 (c)(1),
(2) Date: Feb. 28, 2019

(87) PCT Pub. No.: WO2018/043420
PCT Pub. Date: Mar. 8, 2018

(65) Prior Publication Data
US 2019/0219490 A1    Jul. 18, 2019

(30) Foreign Application Priority Data

Aug. 29, 2016 (JP) .............................. JP2016-167162
Apr. 17, 2017 (JP) .............................. JP2017-081596

(51) Int. Cl.
*G01N 11/14* (2006.01)
*G01N 33/86* (2006.01)
(Continued)

(52) U.S. Cl.
CPC ........... *G01N 11/14* (2013.01); *G01N 33/483* (2013.01); *G01N 33/49* (2013.01); *G01N 33/86* (2013.01)

(58) Field of Classification Search
CPC .................................................... G01N 11/14
See application file for complete search history.

(56) References Cited

U.S. PATENT DOCUMENTS 4,193,293 A    3/1980    Cavallari
4,726,220 A *  2/1988    Feier ................... G01N 11/14
                                                73/54.28
(Continued)

FOREIGN PATENT DOCUMENTS

EP    2208996 A1    7/2010
JP    H9507580 A    7/1997
(Continued)

OTHER PUBLICATIONS

Search Report in International Application No. PCT/JP2017/030773 dated Oct. 31, 2017, 2 pages.
(Continued)

*Primary Examiner* — Paul M. West
*Assistant Examiner* — Mark A Shabman
(74) *Attorney, Agent, or Firm* — Marshall, Gerstein & Borun LLP

(57) ABSTRACT

A blood coagulation test device includes: a container into which a test-object blood is placed; a stirring part for stirring the test-object blood in the container; an elastic body being connected to the stirring part and capable of deforming in response to a force received through stirring of the test-object blood from the stirring part; a control unit for transmitting a predetermined rotary motion to the stirring part and causing the stirring part to rotate in a reciprocating manner in a circumferential direction by rotating the elastic body in a reciprocating manner about an axis of the stirring part as a rotation axis and controlling the reciprocating rotation at a position separated by a predetermined diameter from the rotational axis; and a measurement unit for measuring a rotation angle pertaining to the reciprocating rotation of the stirring part.

11 Claims, 35 Drawing Sheets

(51) Int. Cl.
    *G01N 33/483*   (2006.01)
    *G01N 33/49*    (2006.01)

(56)            References Cited

U.S. PATENT DOCUMENTS

|               |         |                          |
|---------------|---------|--------------------------|
| 5,777,212 A   | 7/1998  | Sekiguchi et al.         |
| 5,777,215 A   | 7/1998  | Calatzis et al.          |
| 2001/0053552 A1* | 12/2001 | Cohen .......... G01N 33/4905 |
|               |         |                  436/69  |
| 2005/0180886 A1 | 8/2005 | Bote Bote                |
| 2009/0004681 A1 | 1/2009 | Hoshiko et al.           |
| 2009/0130645 A1 | 5/2009 | Schubert et al.          |
| 2012/0210774 A1* | 8/2012 | Raffer .............. G01N 11/14 |
|               |         |                  73/54.28 |
| 2016/0091515 A1 | 3/2016 | Gorin et al.             |

FOREIGN PATENT DOCUMENTS

| JP | 2002-082118 A | 3/2002 |
| JP | 2002-537560 A | 11/2002 |
| JP | 2005-523433 A | 8/2005 |
| JP | 2009-008503 A | 1/2009 |
| JP | 2010-217059 A | 9/2010 |
| JP | 2015-090293 A | 5/2015 |

OTHER PUBLICATIONS

Suzuki Nao, Thromboelastography in operating room and ICU, [online], Dec. 15, 2015. Jikei ICU study group. The Internet URL: http://www.jikeimasuika.jp/icu_st/151215.pdf [searched on Jun. 3, 2016], retrieved from the internet on Feb. 26, 2019, 86 pages.

International Preliminary Report on Patentability and Written Opinion in International Application No. PCT/JP2017/030773 dated Mar. 14, 2019, 6 pages.

Sorensen et al., "Whole Blood Coagulation Thrombelastographic Profiles Employing Minimal Tissue Factor Activation", Journal of Thrombosis and Haemostasis, vol. 1, No. 3, Mar. 1, 2003, pp. 551-558.

Extended European Search Report in EP Application No. 17846425.1 dated Apr. 6, 2020, 8 pages.

Office Action in JP Application No. 2018-537268 dated Apr. 6, 2021, 8 pages.

* cited by examiner

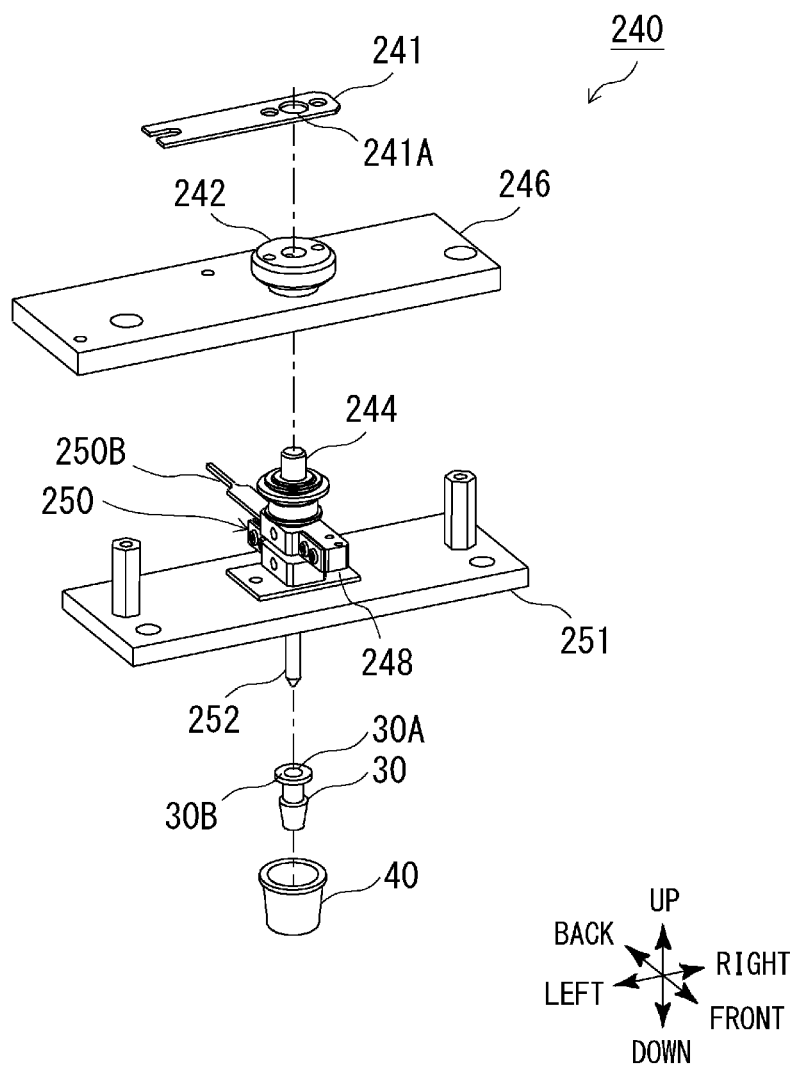

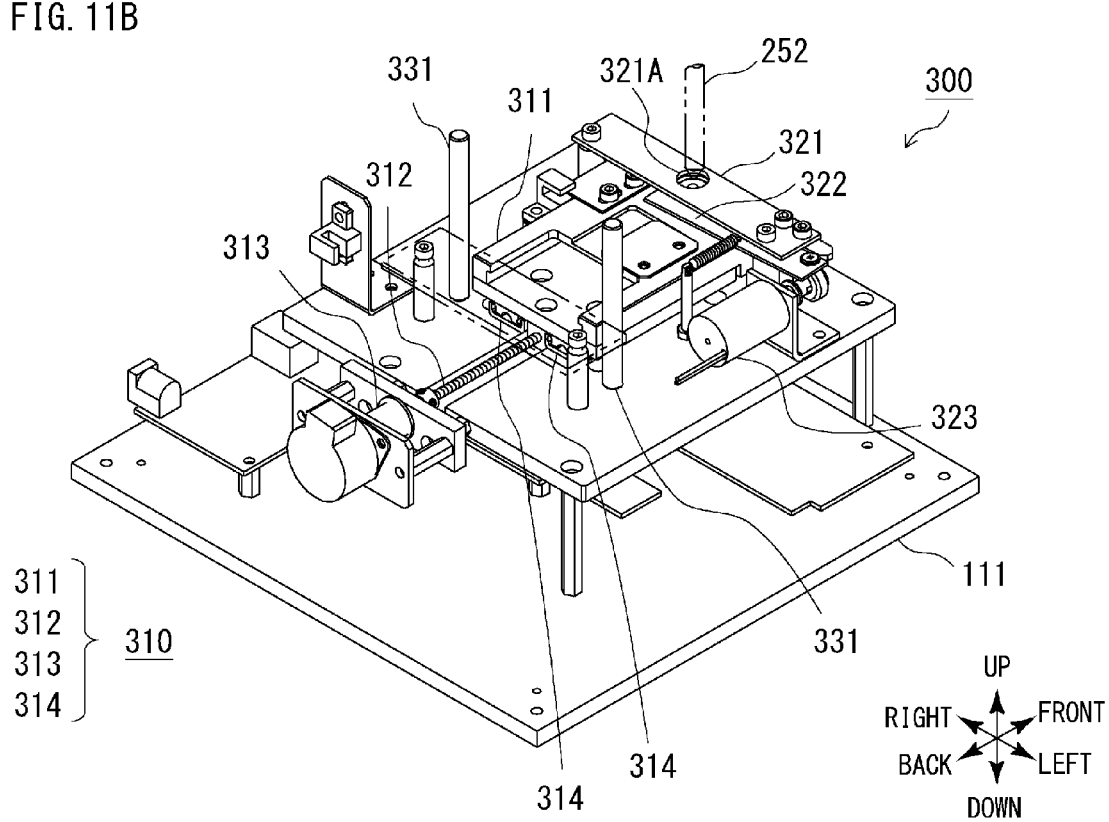

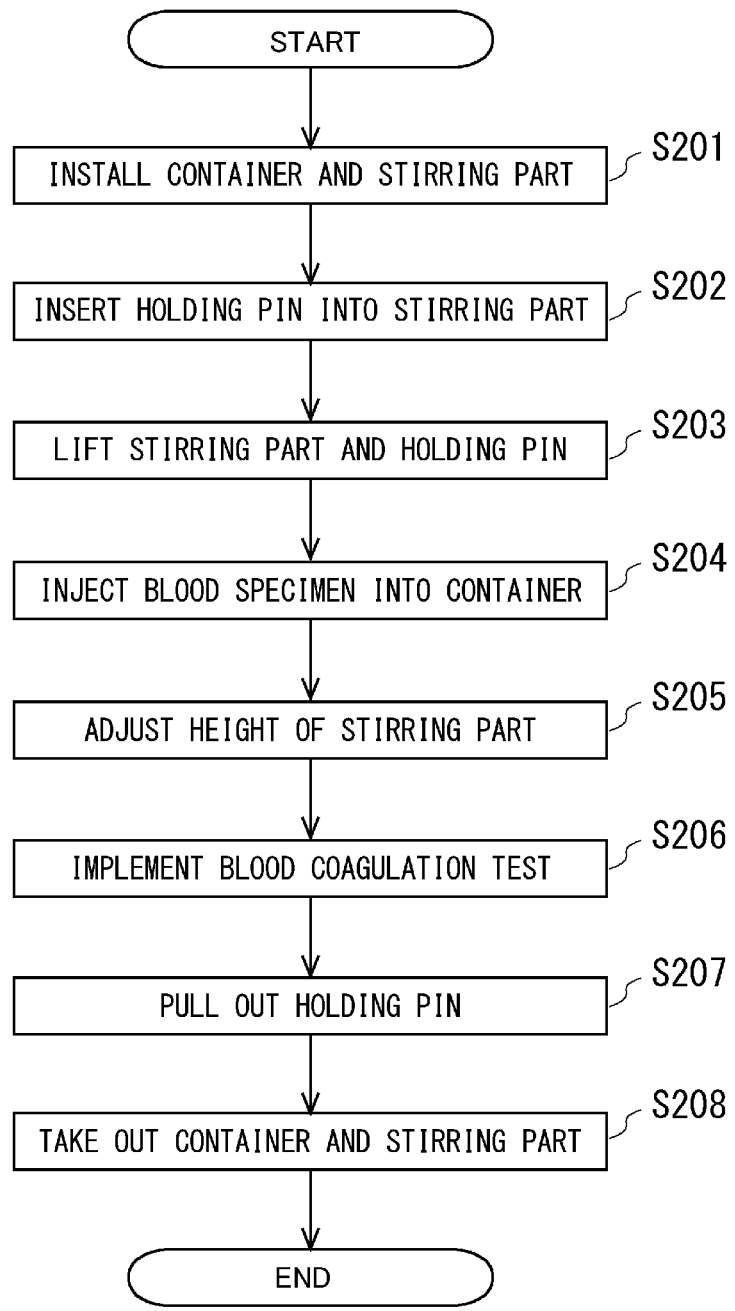

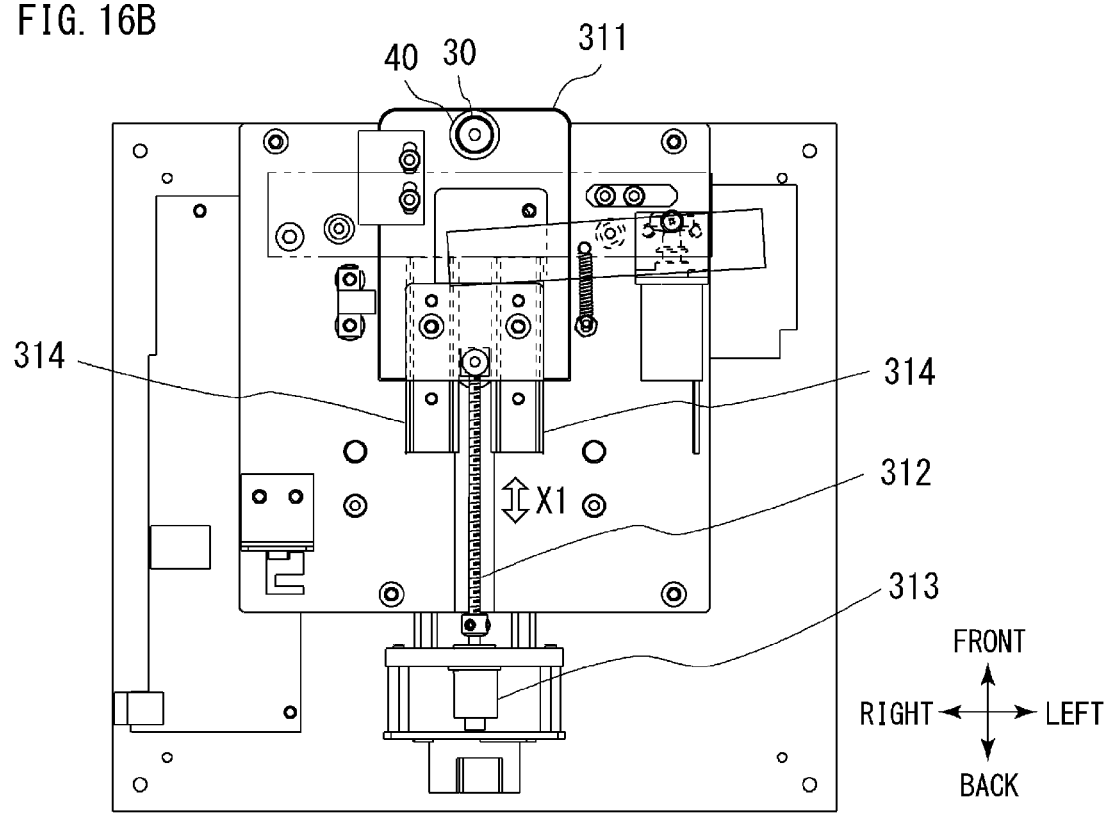

BLOOD COAGULATION TEST DEVICE AND BLOOD COAGULATION TEST METHOD

TECHNICAL FIELD

The present invention relates to a blood coagulation test device and a blood coagulation test method.

BACKGROUND ART

The state of blood coagulation in the process of blood clotting is tested to assess a pathological condition of hemophilia that causes a decrease/loss of blood coagulation factors for solidifying blood upon hemorrhage or other incidents, or to assess the effect of drug such as a hemostatic agent. As a method of testing the state of blood coagulation, for example, an optical test method that detects coagula and measures coagulation time by irradiating light to blood as a test object (hereinafter, also referred to as a blood specimen) to which a reagent has been added and measuring a scattered light quantity (for example, refer to PTL 1) is known. In addition, there is known a method of dynamically testing the state of blood coagulation, such as viscosity, by rotating in a reciprocating manner a pin that is immersed in a cup containing a blood specimen within a certain range of angle (4.75 degrees) and measuring a decrease in the rotation angle of the pin caused by the blood coagulation (for example, refer to NPL 1).

PRIOR ART REFERENCES

Patent Documents

PTL 1: Japanese Unexamined Patent Publication (Kokai) No. 2010-217059

Non-Patent Documents

NPL 1: Suzuki Nao, Thromboelastography in operating room and ICU, [online], Dec. 15, 2015. Jikei ICU study group. The Internet URL: http://www.jikeimasuika.jp/icu_st/151215.pdf [searched on Jun. 3, 2016].

DISCLOSURE OF THE INVENTION

Problems to be Solved by the Invention

When the state of blood coagulation is tested with the optical test method, the measured scattered light quantity may be affected by interference substances in the blood specimen. Further, depending on a difference of test items, that is, a difference of a reagent or the like to be added, a change in the scattered light quantity may not be accurately detected. Since the method is optical, a change in viscoelasticity of the blood is not accurately reflected in the measurement and only data upon completion of blood coagulation is acquired.

Furthermore, with a device for dynamically testing the state of blood coagulation, such as TEG (registered trademark) and ROTEM (registered trademark), measurement conditions such as the rotation angle of a cup in which a blood specimen is injected or of a pin immersed in a blood specimen are not modified according to a difference in the blood specimen, agent, test items, and the like. For example, in TEG, the cup is rotated in a reciprocating manner within a range of 4.45 degrees. However, if the cup is rotated largely over 4.45 degrees after the blood is gelled, the gel may be destroyed and viscoelasticity may not be accurately measured. Further, for example, in ROTEM, the pin is rotated in a reciprocating manner a certain angle by a spring. The rotation angle transmitted by the spring to the pin is fixed to 4.75 degrees, and the pin gradually stops rotating as the viscoelasticity increases due to blood coagulation. As such, since the rotation angle and rotation speed of the cup or the pin are constant in measurement of a highly viscoelastic area where blood coagulation is advanced or, conversely, in measurement of a low viscoelastic area, a desired resolution cannot be obtained and evaluation of the effect of drug is sometimes difficult. Further, as these devices are expensive, a more compact and lighter-weight device with lower price has been sought.

The object of the present invention is to provide a technique for obtaining a resolution according to a test object in a blood coagulation test.

Means for Solving the Problems

To solve the above-described problem, the present invention transmits a predetermined reciprocating rotary motion to a blood stirring part by rotating in a reciprocating manner an elastic body that is connected to the stirring part with the axis of the stirring part as a rotation axis and controlling the rotation at a position separated by a predetermined diameter from the rotation axis.

Specifically, the blood coagulation test device according to the present invention includes: a container into which test-object blood is placed; a stirring part for stirring the test-object blood in the container; an elastic body being connected to the stirring part and capable of deforming in response to a force received through stirring of the test-object blood from the stirring part; a control unit for transmitting a predetermined reciprocating rotary motion to the stirring part and causing the stirring part to rotate in a reciprocating manner in a circumferential direction by rotating the elastic body in a reciprocating manner about an axis of the stirring part as a rotation axis and controlling the reciprocating rotation at a position separated by a predetermined diameter from the rotational axis; and a measurement unit for measuring the rotation angle pertaining to the reciprocating rotation of the stirring part.

With the above-described blood coagulation test device, the reciprocating rotation of the stirring part can be controlled within a predetermined angle. The control unit is, for example, a servo motor of which miniaturization and mass production have been promoted for control of a tail or the like of a radio control airplane, control of the direction of a drone camera, or the like. The servo motor is a motor that includes a servo mechanism for automatically controlling the position, direction, speed of an object to achieve target values. As such, the servo motor can accurately control a rotation at a low speed and a rotation of a desired angle. Thus, in a blood coagulation test, the blood coagulation test device can obtain a resolution according to a test object by properly controlling a rotation speed and a rotation angle to be transmitted to the stirring part. In addition, with a compact, light-weight, and low-priced servo motor, costs of a blood coagulation test can be suppressed. Further, instead of stirring a plurality of blood specimens by the same control, a servo motor is controlled for each blood specimen, thereby realizing a test that is appropriate to each blood specimen. Note that the reciprocating rotary motion is movement of rotation within a range of a predetermined rotation angle about a rotation axis.

The rotation angle of the stirring part can be analyzed by capturing images using a camera or the like equipped on a measurement unit. Specifically, for example, a pinhole or the like may be provided at a position where the rotation of the stirring part can be measured, and the rotation angle of the stirring part may be analyzed based the imaged movement of the pinhole or the like. Alternatively, the rotation angle of the stirring part can be analyzed by position analysis of a non-contact encoder. The encoder is a sensor that converts a dynamic change in position into information indicating a rotary position or a linear displacement position and outputs as electrical signals.

Note that the control unit may change a predetermined reciprocating rotary motion according to a rotation angle measured by the measurement unit. With such a blood coagulation test device, for example, when coagulation of blood advances and the rotation of the stirring part has stopped, the viscoelastic state of the highly viscous blood can be accurately analyzed by enlarging the rotation angle of the predetermined reciprocating rotary motion that is transmitted from the servo motor to the stirring part.

Further, the predetermined reciprocating rotary motion may be a reciprocating rotary motion in a circumferential direction within a range of a certain angle. For example, for analysis of a low viscoelastic area, the resolution can be improved by setting an angle smaller than a certain angle so as to maximize the sensitivity (sensitivity to a subtle change in blood viscoelasticity) of the spring. In addition, as the viscoelasticity gradually increases, the resolution in high viscosity can be improved by enlarging the rotation angle. As such, the state of coagulation can be tested according to a blood specimen or a test-object agent by changing the angle that is set as a constant angle. Further, the rotation angle can be changed according to a target in the middle of measurement. For example, the reciprocating motion of 4.75 degrees may be set in the process of blood coagulation, and, when the viscoelasticity has reached to a certain level, the rotation angle may be enlarged to analyze fibrynosis (thrombolysis). In this way, a sharper thrombolytic process can be analyzed.

Further, the control unit may control a predetermined reciprocating rotary motion so that the rotation angle of the stirring part becomes constant. With such a blood coagulation test device, the state of blood coagulation can be tested based on a change in the rotational rate or the like of the servo motor as an example of the control unit.

Alternatively, the measurement unit may correct the rotation angle when the test-object blood is stirred using the elastic body, based on a difference between a first rotation angle that is measured by the measurement unit when a predetermined solution is stirred using the elastic body and a second rotation angle that is measured by the measurement unit when the predetermined solution is stirred using a reference elastic body as a reference for the elastic body. With such a blood coagulation test device, variation in energized force or the like among elastic bodies can be adjusted and the influence of a difference of an elastic body in use on the measurement result can be mitigated.

Note that the predetermined solution may be a solution of a gelling agent, such as agarose and gelatin. The predetermined gelation temperature is preferably in a range of 34.5 to 37.5° C. Coagulation start time can be adjusted by changing a temperature of the predetermined solution at the start of measuring, and viscoelasticity during gelation can be adjusted by changing the concentration of the predetermined solution. In this way, by changing the temperature and concentration of the predetermined solution at the start of measuring, data for correcting a measurement result for each elastic body can be obtained according to a variety of conditions of viscoelasticity upon coagulation start time and during gelation. By calibrating the measurement result based on the obtained data, variations among springs and devices can be corrected.

Note that the present invention can be viewed from a perspective of method. For example, the present invention includes: a stirring step for stirring test-object blood that is placed in a container by a stirring part; a control step for transmitting a predetermined rotary motion to the stirring part and causing the stirring part to rotate in a reciprocating manner in a circumferential direction by rotating an elastic body in a reciprocating manner about an axis of the stirring part as a rotational axis and controlling the reciprocating rotation at a position separated by a predetermined diameter from the rotational axis, the elastic body being connected to the stirring part and capable of deforming in response to a force received through stirring of the test-object blood from the stirring part; and a measurement step for measuring a rotation angle pertaining to the reciprocating rotation of the stirring part.

Effect of the Invention

According to the present invention, a resolution according to each test object can be obtained in a blood coagulant test.

BRIEF DESCRIPTION OF THE DRAWINGS

FIG. 10B is a partial exploded view of the stirring motion transmission mechanism and a perspective view of a container;

FIG. 11B is a perspective view when the lower unit is viewed from a left back side;

FIG. 15 is a flowchart exemplifying the flow of the operation of the blood coagulation test device according to the second embodiment;

FIG. 16B is a diagram illustrating a state where the placing table is slid to the front side and a container can be installed on the placing table;

EMBODIMENTS FOR CARRYING OUT THE INVENTION

The following will describe embodiments of the present invention with reference to the drawings. The configurations of the following embodiments are examples and the present invention is not limited to the configuration of the embodiments.

Embodiments

Figure 1:
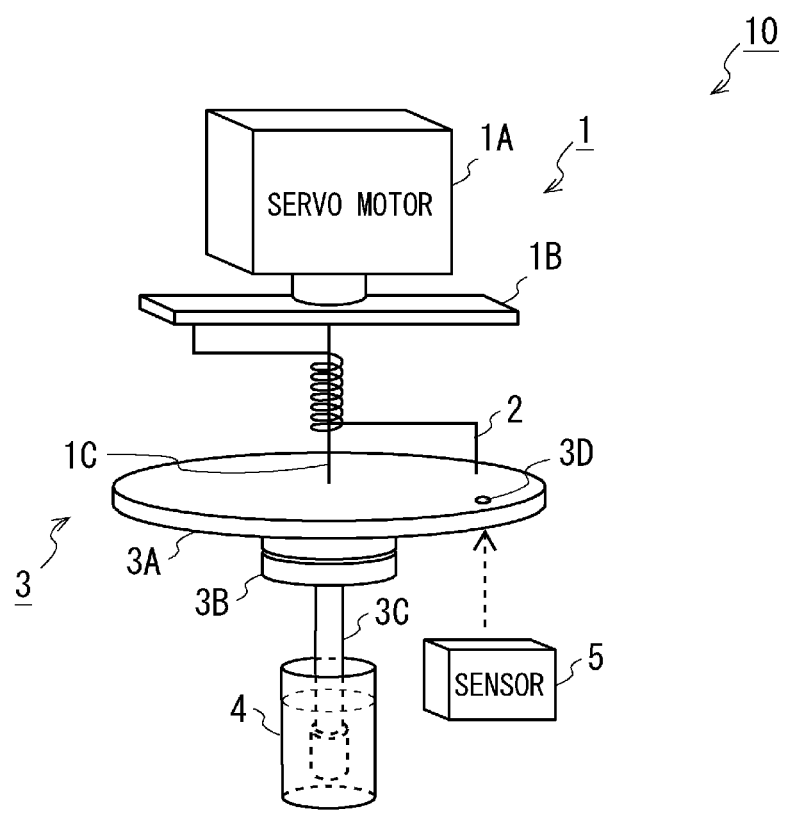
FIG. 1 is a schematic diagram exemplifying a configuration of a blood coagulation test device.

FIG. 1 is a schematic diagram exemplifying a configuration of a blood coagulation test device. The blood coagulation test device 10 includes a control unit 1, an elastic body 2, a stirring part 3, a container 4 and a sensor 5. The blood coagulation test device 10 stirs a blood specimen placed in the container 4 by the stirring part 3 through the elastic body 2 under the control of the control unit 1. Then, the blood coagulation test device 10 measures the state of blood coagulation or the like by calculating the rotation angle of the stirring part 3 from images captured by the sensor 5. The blood coagulation test device 10 includes a control device, not illustrated, that controls the processing of the control unit 1 and the sensor 5.

The control unit 1 receives a command from the control device and drives a reciprocating rotary motion of the stirring part 3 through the elastic body 2. In FIG. 1, the control unit 1 includes a servo motor 1A, an elastic body support part 1B, and an elastic body support shaft 1C. The servo motor 1A causes the elastic body support part 1B to perform a predetermined reciprocating rotary motion about the axis of the stirring part 3 as the rotation axis. The predetermined reciprocating rotary motion is, for example, a reciprocating rotary motion within a range of a certain angle. The predetermined reciprocating rotary motion may be movement that is controlled in such a way that the rotation angle of the stirring part 3 is constant. That is, the servo motor 1A controls the rotation angle of the stirring part 3 to be constant by changing the rotation angle according to the coagulation state of a blood specimen.

The elastic body support part 1B performs a predetermined reciprocating rotary motion that is driven by the servo motor 1A. Further, the elastic body support part 1B supports the elastic body 2 and transmits the predetermined reciprocating rotary motion to the elastic body 2. The elastic body support shaft 10 supports the elastic body 2 as a rotation axis of a predetermined rotary motion that is transmitted to the elastic body 2 from the elastic body support part 1B.

Note that the configuration of the control unit 1 is not limited to the example of FIG. 1. As long as the control unit 1 can support the elastic body 2, transmit a predetermined reciprocating rotary motion to the elastic body 2, and control the reciprocating rotary motion at a position separated by a predetermined diameter from the rotation axis, for example, the control unit 1 may support two wire springs as the elastic body 2 at both ends of the elastic body support part 1B.

The elastic body 2 transmits the predetermined reciprocating rotary motion transmitted from the elastic body support part 1B to the stirring part 3. Further, when blood coagulation advances and the stirring part 3 has come to stop following the predetermined reciprocating rotary motion any more, the elastic body 2 can be deformed in response to a force in a circumferential direction of the rotation axis received from the stirring part 3. In the example of FIG. 1, a coil spring is disposed at a position where the elastic body 2 is supported by the elastic body support shaft 10. The coil spring can be deformed in response to a force received from the stirring part 3.

Note that the elastic body 2 may not be limited to the example of FIG. 1. As long as the elastic body 2 can transmit the predetermined reciprocating rotary motion to the stirring part 3 and be deformed in response to a force received from the stirring part 3, for example, a wire spring may be used instead of a coil spring. Alternatively, the elastic body 2 may be configured by a plurality of elastic bodies.

The stirring part 3 stirs the blood specimen in the container 4 by the predetermined reciprocating rotary motion that is transmitted from the control unit 1 through the elastic body 2. When the blood coagulation advances, the rotation angle of the stirring part 3 becomes smaller than the rotation angle pertaining to the predetermined reciprocating rotary motion. In FIG. 1, the stirring part 3 includes a rotation transmission part 3A, a bearing 3B, a stirring pin 3C, and a pinhole 3D.

The rotation transmission part 3A is connected to the elastic body 2 and transmits the predetermined reciprocating rotary motion transmitted from the elastic body 2 to the stirring pin 3C. The rotation transmission part 3A can rotate, in a reciprocating manner, in a circumferential direction about the axis of the stirring pin 3C as a rotation axis. The rotation transmission part 3A is connected to the elastic body 2 at a position that is separated by a predetermined diameter from the rotation axis and the rotation is controlled at the position. Since the rotation angle can be easily adjusted by controlling the rotation at a position separated from the rotation axis, the rotation transmission part 3A can accurately transmit the predetermined reciprocating rotary motion to the stirring pin 3C.

Note that, while, in FIG. 1, the rotation transmission part 3A is a disc shaped member that is disposed perpendicular to the axis of the stirring pin 3C, the shape of the rotation transmission part 3A is not limited to the disc shape. The rotation transmission part 3A may be disposed on top of the axis of the stirring pin 3C and connected to the elastic body 2 at a position separated from the rotation axis by a predetermined diameter.

The bearing 3B supports the reciprocating rotation of the stirring pin 3C. Although in FIG. 1 the bearing 3B is a magnetic bearing of a ring magnet, the bearing 3B may be a rolling bearing such as ball bearing or an air bearing. When a magnetic bearing is used as the bearing 3B, the friction of the bearing part is reduced and the rotation transmission part 3A can transmit a more precise reciprocating rotary motion to the stirring pin 3C.

The stirring pin 3C is immersed in the container 4 and stirs the blood specimen in the container 4 by the predetermined reciprocating rotary motion that is transmitted from the rotation transmission part 3A. When the blood coagulation advances in the container 4, a reaction force against the predetermined reciprocating rotary motion makes the rotation angle of the stirring pin 3C small. Further, since the rotation transmission part 3A rotates in a reciprocating manner in conjunction with the stirring pin 3C, the rotation angle of the rotation transmission part 3A becomes small in the same way as the stirring pin 3C. When the movement of the rotation transmission part 3A has come to stop following the predetermined reciprocating rotary motion transmitted from the elastic body 2, the elastic body 2 deforms in response to a force in the opposite direction to the predetermined reciprocating rotary motion.

The pinhole 3D serves as a mark indicating a reference position of the rotation transmission part 3A. By detecting and analyzing the movement of the pinhole 3D by the sensor 5, the rotation angle of the rotation transmission part 3A, in other words, the rotation angle of the stirring pin 3C can be measured. In FIG. 1, the pinhole 3D is a hole provided at a position separated from the rotation axis of the rotation transmission part 3A. The sensor 5 (for example, a camera) detects incident light through the pinhole 3D and measures the rotation angle of the stirring pin 3C from the movement of the pinhole 3D. The rotation angle can be calculated based on the length of the diameter from the rotation axis to the pinhole 3D and the moved distance of the pinhole 3D detected by the sensor 5.

Note that the pinhole 3D is not limited to a hole provided at the rotation transmission part 3A. For example, the pinhole 3D may be a recess or a projection provided at a position detectable by the sensor 5. In such a case, the sensor 5 can measure the rotation angle of the stirring pin 3C by analyzing the image of the recess or projection. That is, the pinhole 3D may be any form detectable by the sensor 5 as a mark indicating the reference position.

The container 4 is injected with a blood specimen. The container 4 is arranged so that the stirring pin 3C does not contact the inside of the container 4 during the reciprocating rotation of the stirring pin 3C.

The sensor 5 detects the movement of the pinhole 3D and measures the rotation angle of the stirring pin 3C. Specifically, the sensor 5 may capture an image of the pinhole 3D and transmit the image to the control device, so that the control device can calculate the rotation angle of the stirring pin 3C. The information of the calculated rotation angle may be displayed on the display unit 17.

Note that the sensor 5 may be an electronic device, such as a smartphone or a tablet terminal. In such a case, the electronic device can capture an image of the movement of the pinhole 3D by a camera or the like of the electronic device and calculate the rotation angle of the stirring pin 3C by analyzing the captured image. The electronic device may serve as a control device and control processing of the control unit 1 and the sensor 5.

Configuration of Control Device

Hardware Configuration

Figure 2:
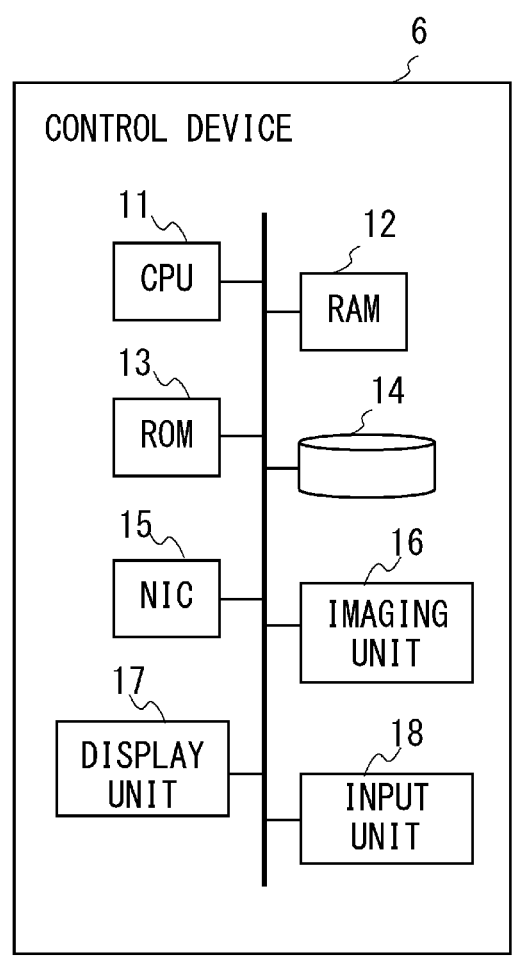
FIG. 2 is a diagram exemplifying a hardware configuration of a control device according to an embodiment.

FIG. 2 is a diagram exemplifying a hardware configuration of the control device according to the embodiment. The control device 6 is a computer including a central processing unit (CPU) 11, a random access memory (RAM) 12, a read only memory (ROM) 13, an auxiliary storage device 14 such as a hard disk drive (HDD), a network interface card (NIC) 15 that is connected to the Internet N through a gateway or the like, an imaging unit 16, a display unit 17, and an input unit 18.

The CPU 11 is a central arithmetic processing device and controls the RAM 12, the auxiliary storage device 14, and the like by processing commands and data of a variety of programs that are read on the RAM 12. The RAM 12 is a main memory and is controlled by the CPU 11, and a variety of commands and data are written in and read from the RAM 12. The ROM 13 is of a read only type and, as a main memory, stores a basic input/output system (BIOS) and a firmware. The auxiliary storage device 14 is a non-transitory storage device, and information that is required to be persistent, such as a variety of programs to be loaded on the RAM 12, is written in or read from the auxiliary storage device 14.

The imaging unit 16 is a camera with an image sensor, such as charge coupled devices (CCDs) and complementary metal oxide semiconductors (CMOS's). When the imaging unit 16 uses the control device 6 as the sensor 5 of FIG. 1, the imaging unit 16 detects the movement of the pinhole 3D of the stirring part 3.

The display unit 17 displays information and the like based on the rotation angle of the measured stirring part 3. The display unit 17 is, for example, a liquid crystal display (LCD). The input unit 18 receives input of information for identifying the elastic body to be used in a test, information relating to a control method of the servo motor 1A, and the like. The input unit 18 is a pointing device, such as a touch pad, a mouse, and a touch panel, a keyboard, an operation button, or the like which accepts an operation input.

Functional Configuration

Figure 3:
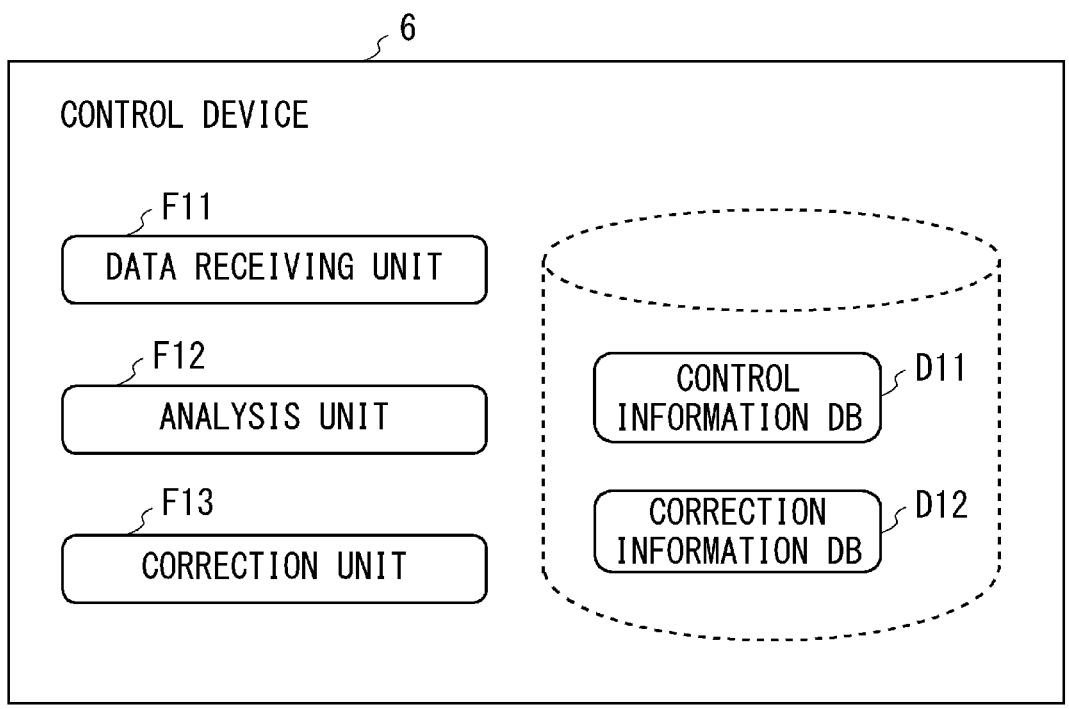
FIG. 3 is a diagram exemplifying a functional configuration of the control device according to the embodiment.

FIG. 3 is a diagram exemplifying a functional configuration of the control device according to the embodiment. The control device 6 functions as a computer including a control information database D11, a correction information database D12, a data receiving unit F11, an analysis unit F12, and a correction unit F13 when a program stored in the auxiliary storage device 14 is read on the RAM 12 and executed by the CPU 11.

Note that, in the embodiment, the functions of the control device 6 are executed by the CPU 11 as a general processor, a part or whole of the functions may be executed by one or a plurality of dedicated processors or the arithmetic circuit of hardware or the like. Here, the arithmetic circuit of hardware is, for example, an adder circuit, a multiplication circuit, a flip flop, and the like formed by combining logic gates. Alternatively, a part or whole of these functions may be executed by a separate computer.

The control information database D11 is a database for storing information for determining an operation pertaining to a predetermined reciprocating rotary motion that is transmitted from the control unit 1 to the stirring part 3. For example, the control information database D11 has a table for storing information for designating a predetermined reciprocating rotary motion by the servo motor 1A, such as information of an angle pertaining to the predetermined reciprocating rotary motion.

The correction information database D12 is a database for storing information relating to calibration for each elastic body 2. The calibration is processing for measuring a deviation of each elastic body 2 from a measurement value of an elastic body as a reference (hereinafter, also referred to as a reference elastic body) and correcting a measurement value based on the measured deviation so as to align the measurement accuracy of each elastic body 2 to the reference elastic body. For example, the correction information database D12 has a table that stores information of a deviation of a measurement value measured for each elastic body 2 from the measurement value of the reference elastic body.

The control information database D11 and the correction information database D12 are constructed when a database management system (DBMS) program executed by the CPU 11 manages data stored in the auxiliary storage device 14. The database management system is, for example, a relational database.

The data receiving unit F11 receives data pertaining to a reciprocating rotary motion of the stirring part 3 detected by the sensor 5. The received data is, for example, image information of the pinhole 3D.

The analysis unit F12 analyzes the data that the data receiving unit F11 received and calculates the rotation angle of the stirring part 3. Further, when the rotation angle of the stirring part 3 is controlled to be constant, the analysis unit F12 generates information used for controlling the servo motor 1A, such as an increase rate of the driving force of the servo motor 1A, based on the calculated rotation angle of the stirring part 3. Information calculated or generated by the analysis unit F12 is stored in the control information database D11.

The correction unit F13 acquires correction information pertaining to a deviation from a reference elastic body from the correction information database D12, and corrects the rotation angle of the stirring part 3 calculated by the analysis unit F12, based on the acquired correction information. The correction information is different for each elastic body 2 to be used. As such, information identifying the elastic body 2 to be used for a test may be input through the input unit 18. The correction unit F13 can acquire correction information pertaining to the elastic body 2 to be used from the correction information database D12 using the input identification information. The information corrected by the correction unit F13 may be displayed on the display unit 17.

Calibration of Elastic Body

The following will describe calibration of the elastic body 2. Even in a test of the same blood specimen, the blood coagulation test device 10 may generate variations in measurement accuracy depending on the elastic body 2 to be used. Thus, the blood coagulation test device 10 defines a reference elastic body as a reference for each elastic body 2 and collects measurement results using a predetermined solution instead of a blood specimen. The blood coagulation test device 10 measures a coagulation state using a predetermined solution for each elastic body 2 and collects a difference from a measurement result using the reference elastic body as correction information. The collected measurement result and correction information of the reference elastic body are stored in the correction information database D12. The blood coagulation test device 10 can correct the detected data for each elastic body 2, based on the correction information stored in the correction information database D12. The predetermined solution is, for example, a solution of agarose, gelatin, or the like.

Figure 4:
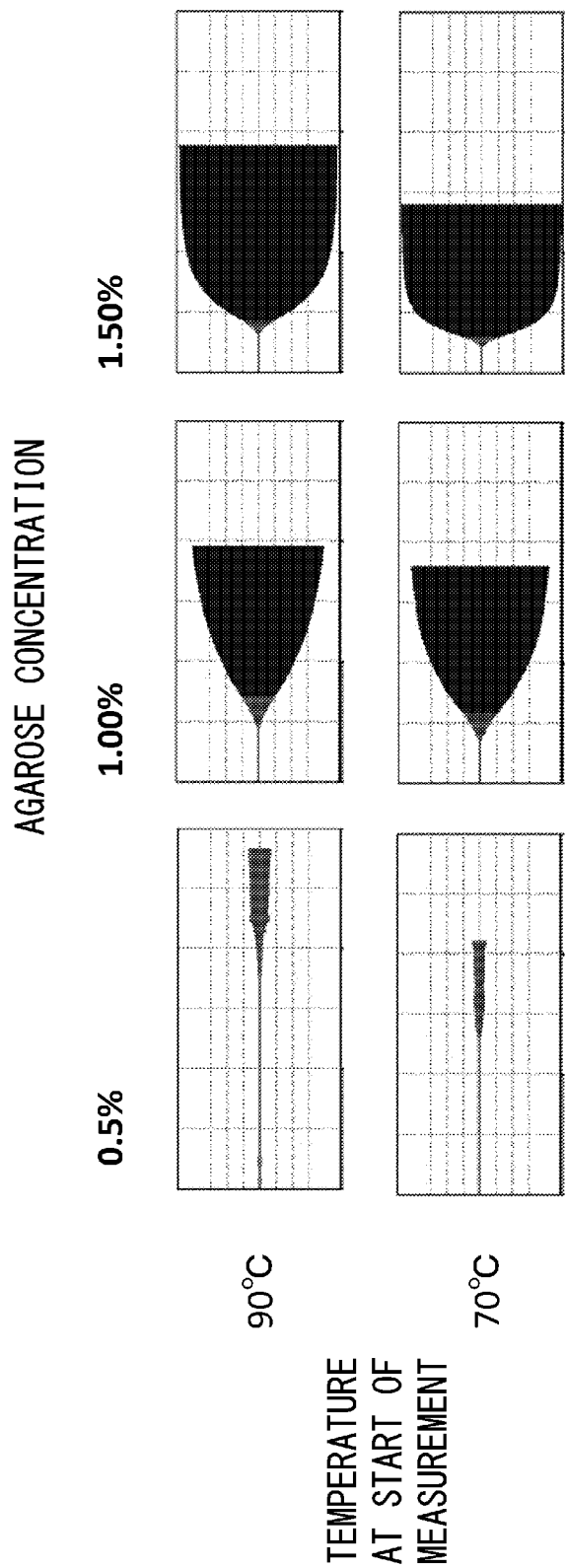
FIG. 4 is diagram illustrating changes in the coagulation state of agarose solutions.

FIG. 4 is diagrams illustrating changes in the coagulation state of agarose solutions. The gelation temperature of agarose is a range of approximately 34.5 to 37.5° C. The vertical axis in each graph illustrated in FIG. 4 indicates a hardness of agarose solution and the shape of the graph expands as the hardness becomes larger. The horizontal axis of each graph indicates time from the start of measurement. FIG. 4 illustrates graphs where concentrations of agarose solutions are 0.5%, 1.0% and 1.5% when the temperature of the agarose solutions upon the start of measurement is 90° C. and when 70° C.

When the concentration of the agarose solution is the same, the start of coagulation is delayed when the temperature upon the start of measurement is 90° C. than when the temperature is 70° C. That is, as the temperature upon the start of measurement becomes higher, the start of coagulation is delayed. Further, when the temperature of agarose solution upon the start of measurement is the same, as the concentration becomes higher, the final gel hardness becomes larger. That is, as the concentration becomes higher, the final gel hardness becomes larger.

The blood coagulation test device 10 can accurately correct variations in measurement results of each elastic body 2 by collecting correction information pertaining to the reference elastic body and each elastic body 2 in a variety of conditions of temperatures and concentrations of agarose solutions upon the start of coagulation.

Flow of Processing

The following will describe the flow of processing of the blood coagulation test device 10 of the present embodiment. In the flow of the processing as herein described, the blood coagulation test device 10 stirs the blood specimen in the container 4 by the stirring part 3 driven by the servo motor 1A and measures the rotation angle of the stirring part 3. Here, the servo motor 1A transmits a predetermined reciprocating rotary motion to the stirring part 3 through the elastic body 2. Further, based on the correction information pertaining to a deviation from the reference elastic body, which is measured in advance for the elastic body 2 to be used, the blood coagulation test device 10 corrects a measurement result. Note that the content and order of the processing, as described below, are examples, and appropriate content and order of processing are preferably employed as necessary in each embodiment.

Figure 5:
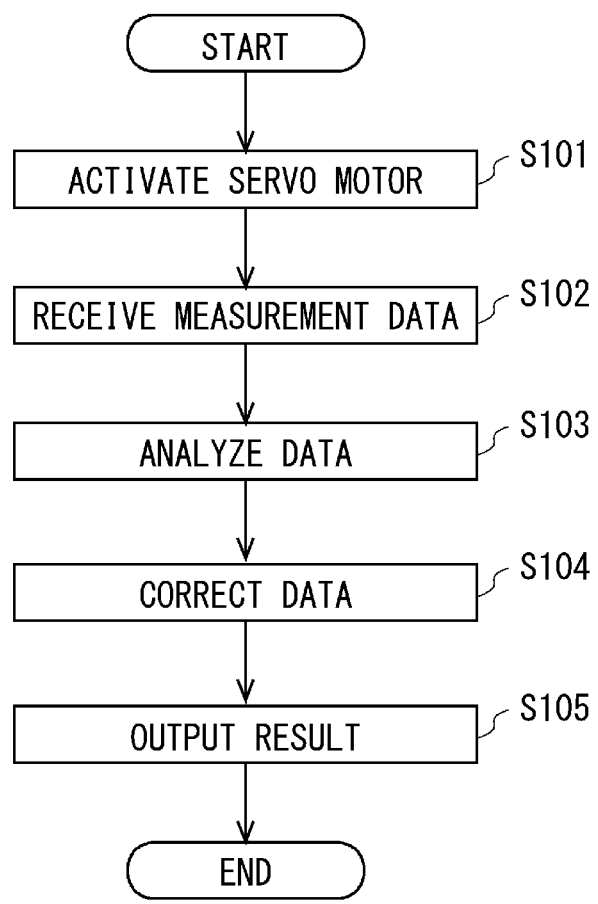
FIG. 5 is a flowchart exemplifying a flow of test processing in the blood coagulation test device.

FIG. 5 is a flowchart exemplifying the flow of test processing in the blood coagulation test device. The flow of processing starts, for example, triggered by injection of a blood specimen and a reagent in the container 4.

First, at step S101, the control device 6 activates the servo motor 1A. The control device 6 controls the servo motor 1A based on information stored in the control information database D11. In accordance with the command of the control device 6, the servo motor 1A transmits a predetermined reciprocating rotary motion to the stirring part 3 through the elastic body 2. The control device 6, for example, may cause the servo motor 1A to transmit the reciprocating rotary motion within a range of a certain angle.

With activation of the servo motor 1A, the stirring part 3 stirs the blood specimen in the container 4. As coagulation of blood advances, the reciprocating rotation of the stirring part 3 has come to stop following the transmitted predetermined reciprocating rotary motion and the rotation angle becomes smaller. The sensor 5 detects the reciprocating rotary motion of the stirring part 3 and transmits data pertaining to the reciprocating rotary motion, such as data of the captured image of the pinhole 3D, to the control device 6.

At step S102, the data receiving unit F11 of the control device 6 receives data transmitted from the sensor 5. At step S103, the analysis unit F12 of the control device 6 calculates the rotation angle of the stirring part 3 by analyzing the received data.

Next, at step S104, the correction unit F13 of the control device 6 corrects the rotation angle calculated by the analysis unit F12. Specifically, the correction unit F13 acquires correction information pertaining to the elastic body 2 in use from the correction information database D12. The correction unit F13 corrects the rotation angle calculated by the analysis unit F12 based on the acquired correction information.

At step S105, the control device 6 outputs data of the rotation angle corrected by the correction unit F13 as a measurement result. The control device 6 can output the measurement result to the display unit 17. The control device 6 may also store the measurement result in the auxiliary storage device 14.

Effects

The blood coagulation test device 10 of the present embodiment can obtain a resolution according to a test object by properly controlling the rotation speed and rotation angle transmitted to the stirring part 3. In addition, with a compact, light-weight, and low-priced servo motor 1A, costs of a blood coagulation test is suppressed. Further, instead of stirring a plurality of blood specimens by the same control, the blood coagulation test device 10 can control the servo motor 1A for each blood specimen, thereby realizing a test that is appropriate to each blood specimen.

Further, when the stirring part 3 has come to stop performing reciprocating rotation as the blood coagulation advances, the blood coagulation test device 10 can analyze the viscoelastic state of the blood of high viscosity by controlling the servo motor 1A to enlarge the rotation angle of the stirring part 3. As such, the blood coagulation test device 10 can acquire data at a predetermined resolution by changing the predetermined reciprocating rotary motion transmitted from the servo motor 1A to the stirring part 3 according to a blood specimen or a test-object agent.

Further, by correcting variations in measurement results for each elastic body 2 in use, based on the correction information that has measured in advance, an influence of a difference of the elastic body 2 in use on the measurement result can be mitigated.

EXAMPLES

The following will describe examples and more specifically describe the present invention. The present invention is not limited to the following examples.

Using the blood coagulation test device 10 according to the embodiment, changes in the coagulation states of blood and an agarose solution were measured. A servo motor WR-ES155 for Petit Robo S2 (manufactured by KYO-HRITSU ELECTRONIC INDUSTRY Co., Ltd.) was used as the servo motor 1A and controlled the reciprocating rotary motion of the pin. For the elastic body 2, a helical torsion spring with the arm angle of 180 degrees, internal diameter of 2 mm, wire diameter of 0.2 mm, material of SUS304-WPB, the number of turns of 3, arm length of 15 mm was used. As for the rotation angle of the pin, the position of a pinhole provided at the rotation transmission part 3A that rotates in a reciprocating manner in conjunction with the pin was detected by a camera (Vktech, 2 m cable, 7 mm USB waterproof endoscope snake camera equipped with 6 LED lights) and the amplitudes of the pin from the positions at both ends of the reciprocating rotation were calculated. The amplitudes of the pin decrease as coagulation of blood or an agarose solution advances. The changes in the coagulation state of the blood and agarose solution were observed by plotting the decreased amounts of amplitudes (also referred to as a clot amplitude, or, simply, amplitude) compared with the amplitudes before the start of coagulation.

Example 1

Figure 6:
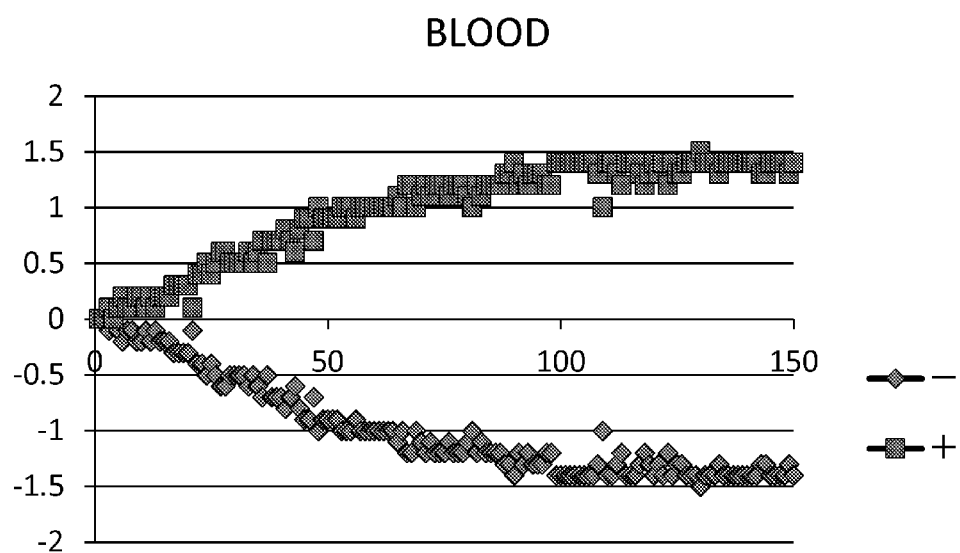
FIG. 6 is a graph illustrating changes in the coagulation state of blood in Example 1.

In Example 1, changes in the blood coagulant state were measured. The blood in the container 4 was measured after adding calcium chloride to the blood collected in a blood collection tube containing 3.2% sodium citrate (TERUMO CORPORATION) at 12 mM final concentration. FIG. 6 is a graph illustrating changes in the coagulation state of the blood in Example 1. The vertical axis of the graph of FIG. 6 indicates the clot amplitude and the horizontal axis indicates time.

The blood coagulation advances from the start time of measurement and the clot amplitude becomes approximately 1 cm in 50 minutes and converges to approximately 1.5 cm in 100 minutes.

Example 2

Figure 7:
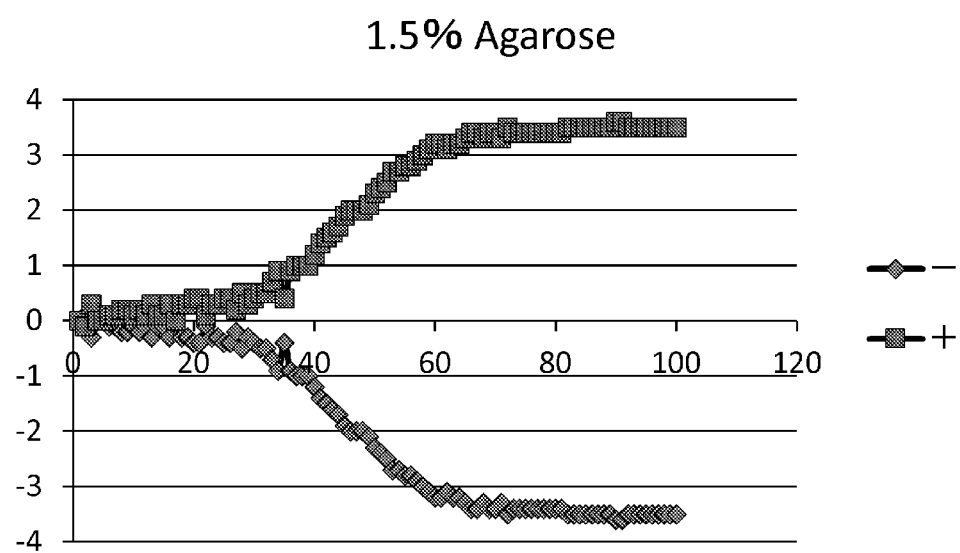
FIG. 7 is a graph illustrating changes in the coagulation state of an agarose solution in Example 2.

In Example 2, changes in the coagulation state of an agarose solution at the concentration of 1.5% were measured. The temperature of the agarose solution at the start time of measurement was approximately 90° C. FIG. 7 is a graph illustrating changes in the coagulation state of the agarose solution in Example 2. The vertical axis of the graph of FIG. 7 indicates the amplitude and the horizontal axis indicates time.

In approximately 20 minutes since the start of measurement, the temperature of the agarose solution became approximately 25° C. and gelation started. In approximately 40 to 60 minutes since the start of measurement, gelation advanced rapidly and converged to the amplitude of approximately 3.5 cm in approximately 80 minutes. From the measurement result of the coagulation state of the agarose solution, it became apparent that the changes in the coagulation state can be accurately measured even when the viscosity is higher than the blood of Example 1.

Second Embodiment

Configuration of Blood Coagulation Test Device According to Second Embodiment

Figure 8A:
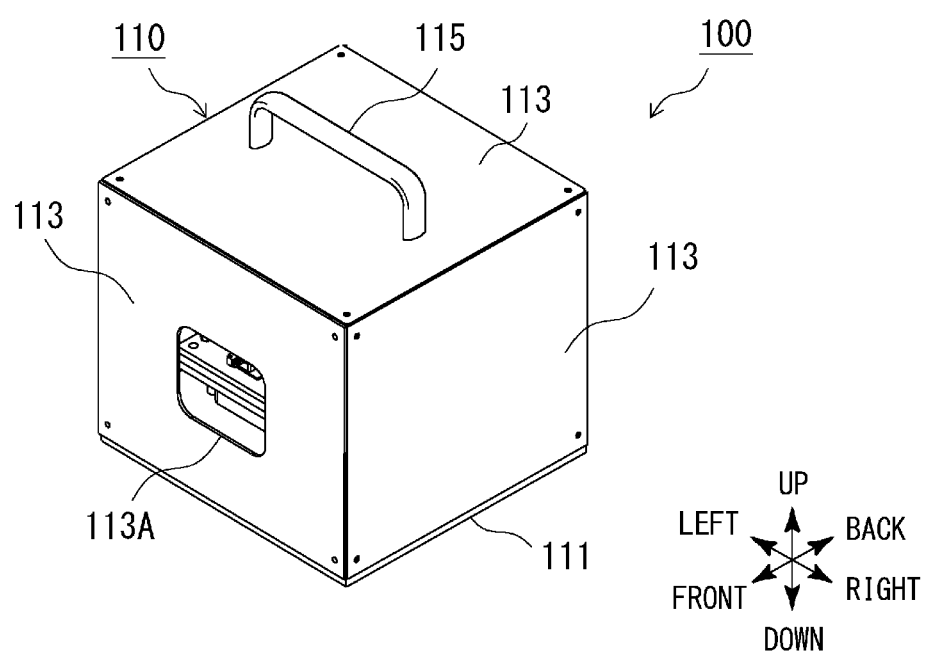
FIG. 8A is a perspective view illustrating the exterior of the blood coagulation test device.
Figure 8B:
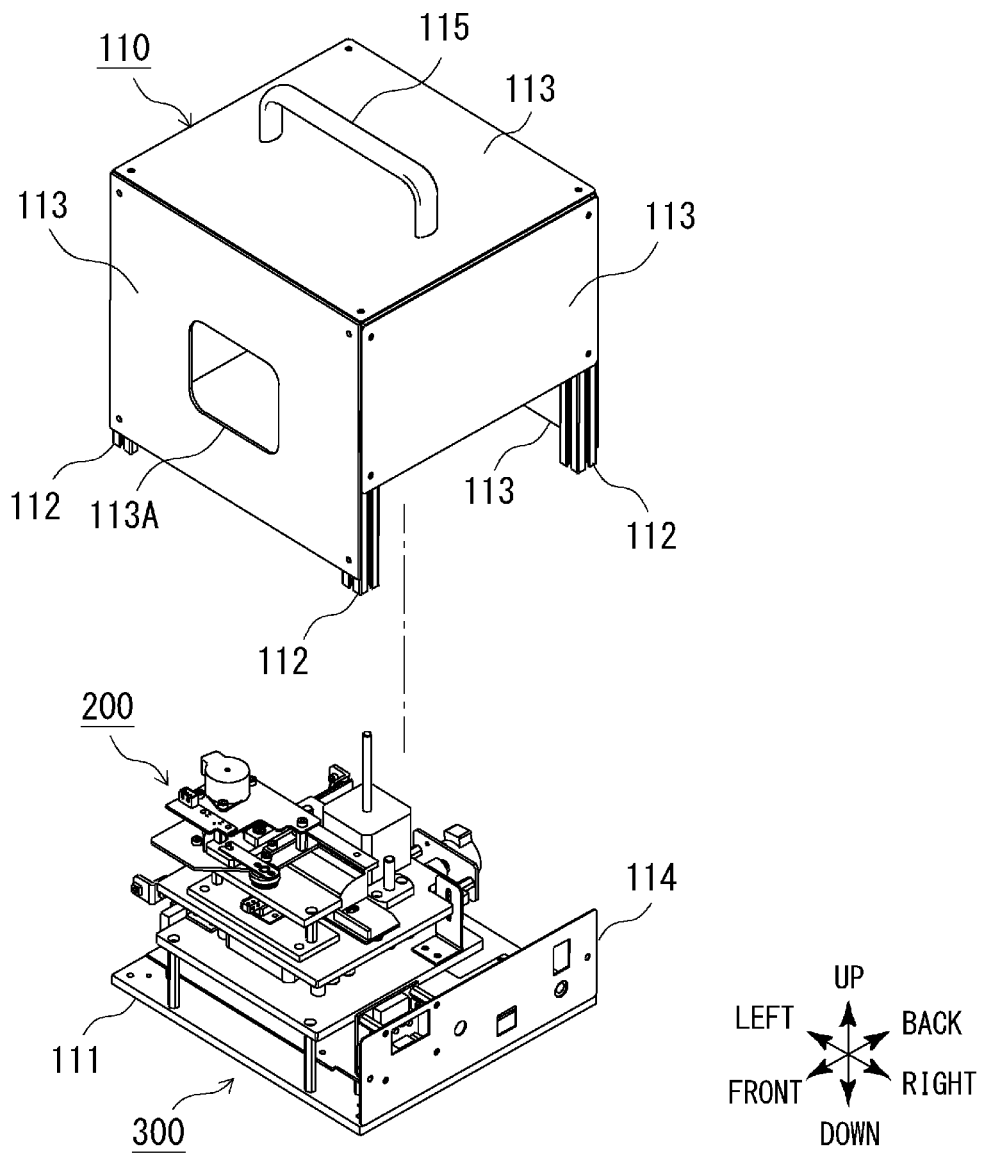
FIG. 8B is a perspective view illustrating the interior of the blood coagulation test device.

FIGS. 8A and 8B illustrate the configuration of the blood coagulation test device according to the second embodiment. FIG. 8A is a perspective view illustrating the exterior of the blood coagulation test device. FIG. 8B is a perspective view illustrating the interior of the blood coagulation test device. The blood coagulation test device 100 includes a case 110, an upper unit 200, and a lower unit 300. Further, the blood coagulation test device 100 includes a control device, not illustrated, which controls the operation of mechanisms of the upper unit 200 and the lower unit 300. The control device according to the second embodiment has the same configuration as the control device 6 according to the above-described embodiment. The operation of mechanisms of the upper unit 200 and the lower unit 300 are driven by commands of the control device according to the second embodiment.

The case 110 is formed in a box shape with a bottom plate 111 of a generally square shape, support pillars 112 that stand at the four corners of the bottom plate 111, panels 113 that are provided on the faces of the front side, back side, upper part of right side, left side, and top side, and a connection panel 114 that is provided on the bottom part of the right side and has an insertion opening through which a cable and the like for connecting with a power source or an external device are inserted. The case 110 houses the upper unit 200 and the lower unit 300. Further, the case 110 includes a handle 115 on the top panel 113 for portability. Further, on the front panel 113, an opening 113A for installing and removing a container containing a blood sample is provided. Note that the blood sample as a test object contains plasma obtained by centrifuging blood or by other means.

As long as the case 110 can house the upper unit 200 and the lower unit 300 and have an insertion opening for connecting each unit to a power source or an external device and an opening that enables installing and removing a container containing a blood specimen, the shape of the case 110, the position and shape of an insertion opening for a cable or the like, and the position and shape of the opening for installing and removing the container are not limited to an example of FIGS. 8A and 8B. The case 110 may be formed, for example, by integrally combining the plurality of panels 113 and support pillars 112 as one member that houses the upper unit 200 and the lower unit 300. Further, instead of providing the handle 115 on the top panel 113, the case 110 may have recesses on the left and right side panels or on the front and back panels 113 for gripping the blood coagulation test device 100 with both hands.

Figure 9A:
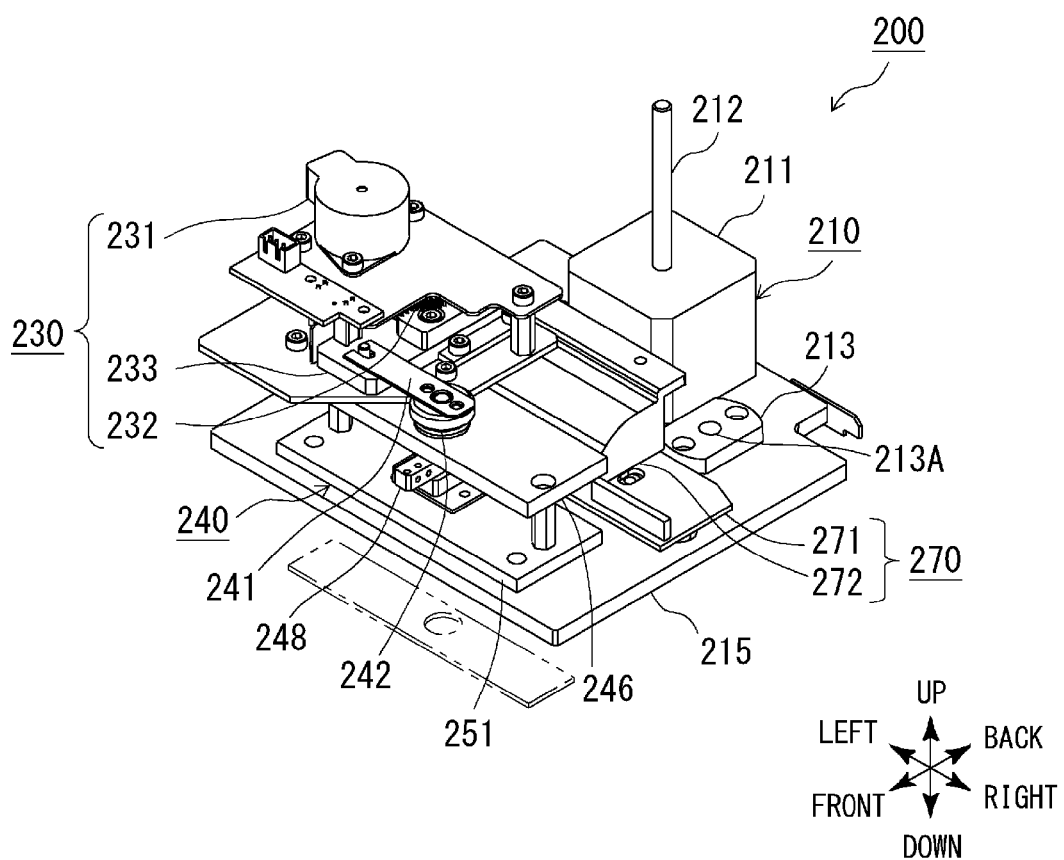
FIG. 9A is a perspective view when an upper unit is viewed from above.
Figure 9B:
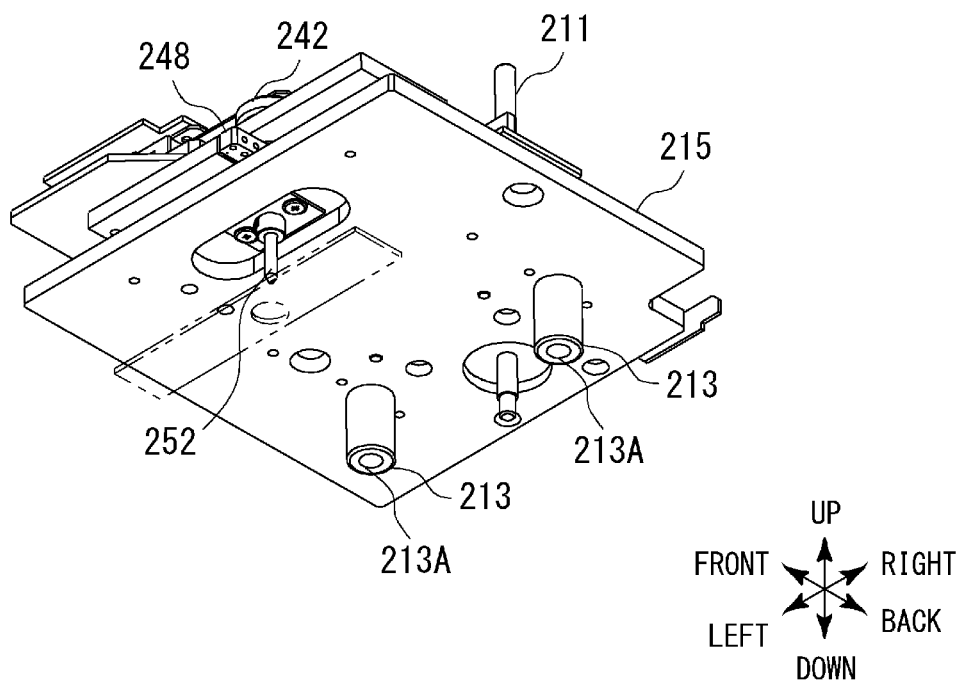
FIG. 9B is a perspective view when the upper unit is viewed from below.

FIGS. 9A and 9B illustrate the configuration of the upper unit 200. FIG. 9A is a perspective view when the upper unit 200 is viewed from above. FIG. 9B is a perspective view when the upper unit 200 is viewed from below. The upper unit 200 includes a lifting mechanism 210, a stirring control mechanism 230, a stirring motion transmission mechanism 240, and a rotation angle measurement mechanism 270.

The lifting mechanism 210 includes a lifting motor 211, a shaft 212, and support shaft guides 213. The lifting motor 211 has thereinside, for example, a female screw in which a full thread shaft 212 is screwed. The female screw is rotatable about the shaft 212 as an axis, driven by the lifting motor 211. The upper unit 200 can be lifted or lowered to a desired height through rotation of the female screw. The support shaft guides 213 are equipped with support shaft insertion holes 213A through which support shafts (not illustrated) are inserted so that the lower unit 300 supports the upper unit 200. As illustrated in FIG. 9B, the support shaft guides 213 have cylindrical portions on the lower side of the upper unit bottom plate 215, and the support shafts are inserted through the support shaft insertion holes 213A. By inserting the support shafts into the support shaft guides 213, the upper unit 200 can be lifted or lowered in the vertical direction. Note that in the example of FIG. 9A, the support shaft guides 213 are disposed on the right side and the left side of the lifting motor 211. Without limitation to a case where the support shaft guides 213 are provided at two positions on both right side and left side of the lifting motor 211, for example, the support shaft guides 213 may be provided on diagonally opposing corners of the upper unit bottom plate 215 or at more than two positions.

The stirring control mechanism 230 includes a stirring motor 231, a gear 232, and a sliding plate 233. The stirring motor 231 drives the rotation of the gear 232. The gear 232 converts a rotary motion to a linear motion and slides the sliding plate 233 back and forth. The sliding plate 233 slides forward and backward according to the rotation of the gear 232, and transmits the operation for stirring the blood specimen to the stirring motion transmission mechanism 240. The stirring motion transmission mechanism 240 will be described in details with reference to FIG. 10A.

Figure 10A:
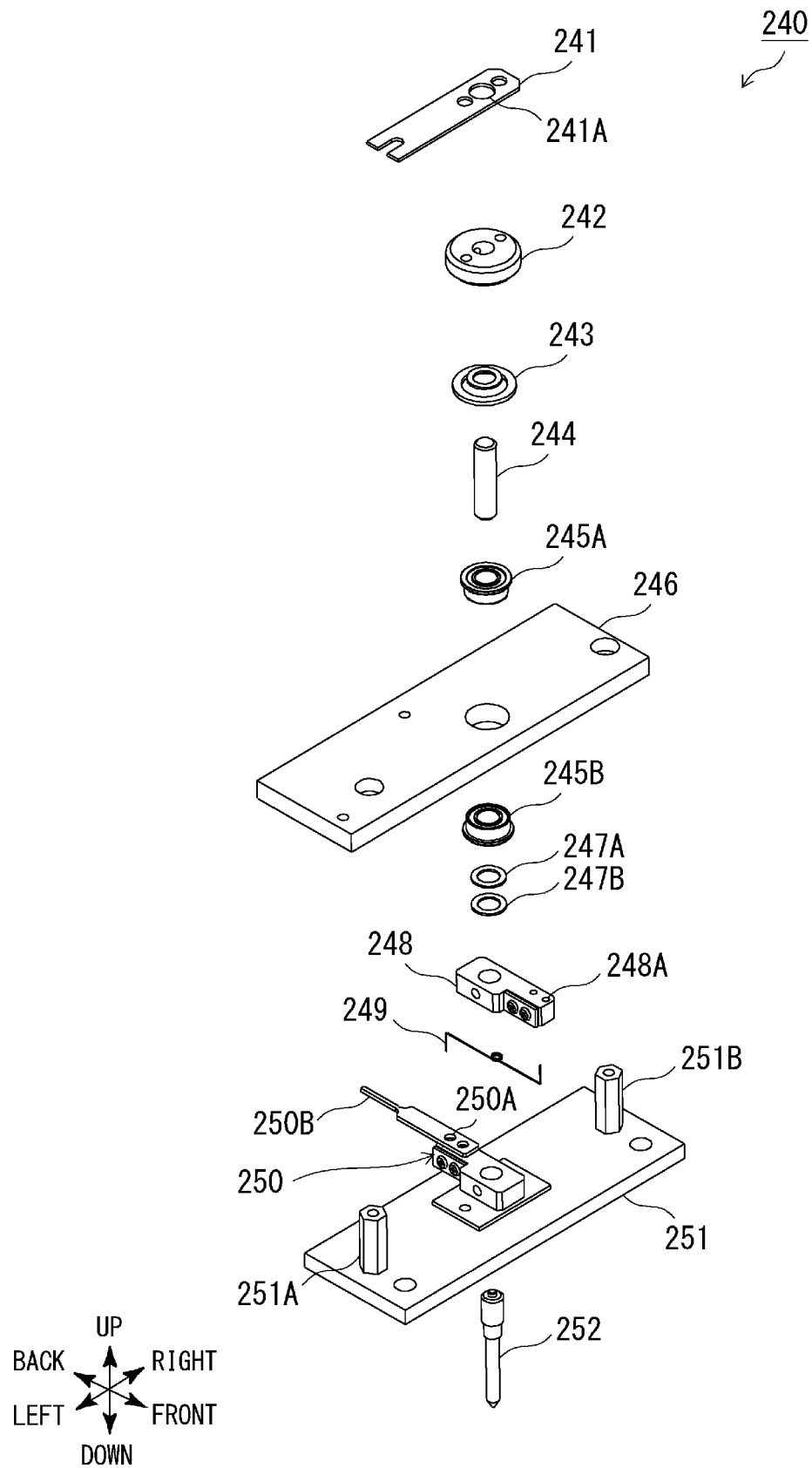
FIG. 10A is an exploded perspective view of a stirring motion transmission mechanism.

FIGS. 10A and 10B illustrate the configuration of the stirring motion transmission mechanism 240. FIG. 10A is an exploded perspective view of the stirring motion transmission mechanism 240. The stirring motion transmission mechanism 240 includes an oscillation plate 241, a rotator 242, a washer 243, a rotation axis 244, a bearing 245A, a bearing 245B, a first base 246, a washer 247A, a washer 247B, an oscillation transmission part 248, an elastic body 249, an oscillation receiving part 250, a second base 251, and a holding pin 252.

The oscillation plate 241 performs a reciprocating rotary motion (hereinafter, also referred to as an oscillatory motion) about the rotation axis 244 that is inserted into the rotation axis insertion hole 241A as an axis according to back-and-forth reciprocating movement of the sliding plate 233. The rotator 242 is fixed to the oscillation plate 241, holds the rotation axis 244 that is inserted in the rotation axis insertion hole 241A, and transmits the oscillatory motion of the oscillation plate 241 to the rotation axis 244. The washer 243 suppresses friction between the rotator 242 and the bearing 245A caused by the oscillatory motion of the rotator 242. The rotation axis 244 is rotatably supported by the bearing 245A and the bearing 245B that is engaged with the bearing 245A. The bearing 245A and the bearing 245B are engaged with each other with the first base 246 interposed therebetween. The stirring control mechanism 230 is placed on the first base 246. The rotation axis 244 is coupled with the oscillation transmission part 248 through the washers 247A and 247B.

The oscillation transmission part 248 oscillates in conjunction with the oscillatory motion of the oscillation plate 241. The oscillation transmission part 248 includes an elastic body coupling part 248A to couple with the elastic body 249. The elastic body 249 uses a coil spring with an axis in the vertical direction in the example of FIG. 10. An end of the elastic body 249 is coupled with the elastic body coupling part 248A and the other end of the elastic body 249 is coupled with the oscillation receiving part 250. The oscillation receiving part 250 includes an elastic body coupling part 250A to couple with the elastic body 249. The other end of the elastic body 249 is coupled with the elastic body coupling part 250A. The oscillation receiving part 250 further transmits the oscillatory motion transmitted through the elastic body 249 to the holding pin 252. The oscillation receiving part 250 includes an oscillation measurement pin 250B for measuring the rotation angle of the oscillatory motion of the oscillation receiving part 250. The rotation angle of the oscillation measurement pin 250B is measured by the rotation angle measurement mechanism 270 illustrated in FIG. 9A. The oscillation receiving part 250 is placed on the second base 251. The second base 251 includes base supporting parts 251A and 251B to support the first base 246. The holding pin 252 is coupled with the oscillation receiving part 250 through the insertion hole (not illustrated) provided on the second base 251. The holding pin 252 oscillates in conjunction with the oscillatory motion of the oscillation receiving part 250.

FIG. 10B is a partial exploded view of the stirring motion transmission mechanism 240, as well as, a perspective view of the container. The members between the oscillation plate 241 and the holding pin 252 illustrated in FIG. 10A are assembled as illustrated in FIG. 10B. The holding pin 252 holds the stirring part 30 and oscillates the stirring part 30 to stir a blood specimen in the container 40. The holding pin 252 is inserted into the holding pin insertion hole 30A provided on top of the stirring part 30. The stirring part 30 rotates in conjunction with the holding pin 252 and stirs the blood specimen in the container 40. Coagulation of the blood specimen in the container 40 generates a force to suppress the oscillation of the holding pin 252, and the rotation angle of the holding pin 252 increases/decreases according to the viscosity of the blood specimen in the container 40. Further, the stirring part 30 includes a flange 30B. The flange 30B is used when the blood coagulation test has ended and the holding pin 252 is pulled out from the stirring part 30. By lifting the holding pin 252 while holding the flange 30B, the holding pin 252 can be pulled out from the stirring part 30.

The rotation angle measurement mechanism 270 in FIG. 9A includes a sensor plate 271 and a light source part 272. The rotation angle measurement mechanism 270 is a mechanism for measuring the rotation angle of the stirring part 30. The sensor plate 271 includes an optical sensor where light receiving elements are linearly disposed. The light source part 272 includes a light source (not illustrated) such as a light emitting diode (LED) that irradiates the optical sensor of the sensor plate 271. In the second embodiment, the rotation angle measurement mechanism 270 detects the rotary motion of the oscillation measurement pin 250B that oscillates above the optical sensor in conjunction with the stirring movement of the blood specimen in the container 40. The rotation angle measurement mechanism 270 can measure the rotation angle of the stirring part 30 that oscillates in conjunction with the oscillation measurement pin 250B by measuring the rotation angle of the oscillation measurement pin 250B. The rotation angle measurement mechanism 270 is an example of the "measurement mechanism." Further, the oscillation measurement pin 250B is an example of a "member to be measured." The blood coagulation test device 100 can accurately measure the rotation angle of the stirring part 30 by measuring, by the rotation angle measurement mechanism 270, the rotation angle of the oscillation measurement pin 250B that oscillates at a position separated from the rotation axis of the stirring part 30.

Figure 11A:
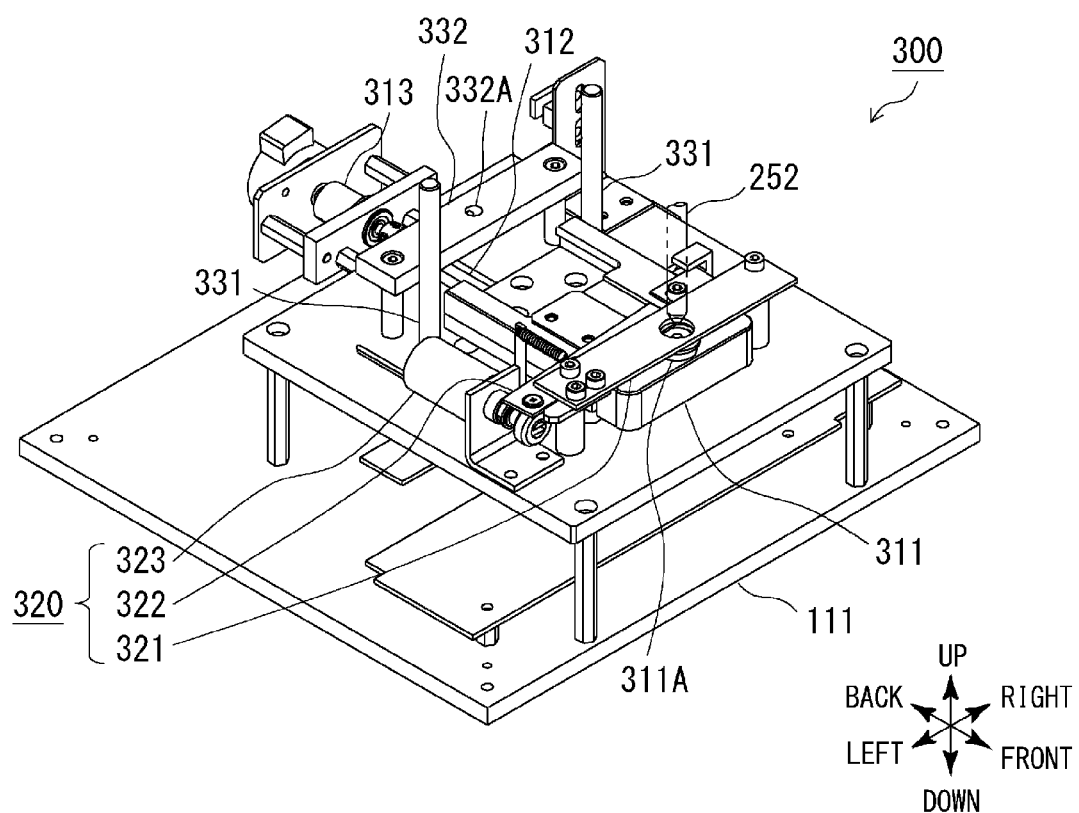
FIG. 11A is a perspective view when a lower unit is viewed from a left front side.

FIGS. 11A and 11B illustrate the configuration of the lower unit 300. FIG. 11A is a perspective view when the lower unit 300 is viewed from the left front side. FIG. 11B is a perspective view when the lower unit 300 is viewed from the left back side. The lower unit 300 includes a placing table slide mechanism 310 and a holding pin pull-out mechanism 320. Further, the lower unit 300 includes support shafts 331 and an upper unit support table 332 to couple with the upper unit 200. The upper unit support table 332 is provided with a fitting hole 332A in which the lower end of the shaft 212 is fitted and fixed. Note that FIGS. 11A and 11B illustrate a state where the lower unit 300 is disposed on the bottom plate 111 of the case 110.

The placing table slide mechanism 310 illustrated in FIG. 11B includes a placing table 311, a ball screw 312, a slide motor 313, and linear guides 314. The placing table 311 includes a container installation part 311A (FIG. 11A) that is a cylindrical recess that can house the container 40. FIG. 11A illustrates a state where the container 40 is installed in the container installation part 311A and the stirring part 30 is housed in the container 40. The ball screw 312 is screwed into the placing table 311 and oscillates the placing table 311 backward and forward through rotation of the ball screw 312. The slide motor 313 drives the rotary motion of the ball screw 312. The linear guides 314 guide a back-and-forth linear motion of the placing table 311. As long as the placing table slide mechanism 310 can convert the rotary motion of the motor to the linear motion and slides the placing table 311 to a position for enabling installation of the container 40, the placing table slide mechanism 310 may be any linear motion mechanism, such as a timing belt, other than the ball screw mechanism. Note that the blood coagulation test device 100 may include a thermal insulation device (not illustrated) for insulating the temperature of the container 40 housed in the placing table 311 so that the thermal insulation device can keep the blood specimen at a constant temperature during the coagulation test.

The holding pin pull-out mechanism 320 illustrated in FIG. 11A includes a guide plate 321, a holding plate 322, and a solenoid 323. The guide plate 321 is disposed on top of the container installation part 311A of the placing table 311, and an opening 321A is provided for inserting the holding pin 252 into the holding pin insertion hole 30A of the stirring part 30. When the holding pin 252 is pulled out from the holding pin insertion hole 30A, the holding plate 322 rotates to a position where the holding plate 322 can hold the flange 30B of the stirring part 30 with the edge that is connected to the solenoid 323 as an axis. When the holding plate 322 holds the flange 30B of the stirring part 30, the holding pin 252 can be pulled out from the holding pin insertion hole 30A. The solenoid 323 is energized until the holding pin 252 is pulled out from the holding pin insertion hole 30A. While the solenoid 323 is energized, the holding plate 322 maintains a state where the holding plate 322 is rotated to a position of holding the flange 30B of the stirring part 30, and the holding pin 252 is pulled out from the stirring part 30. The holding pin pull-out mechanism 320 is an example of the "detachment mechanism." The holding pin 252 is an example of the "holding member." The holding plate 322 is an example of the "press-holding member."

Figure 12:
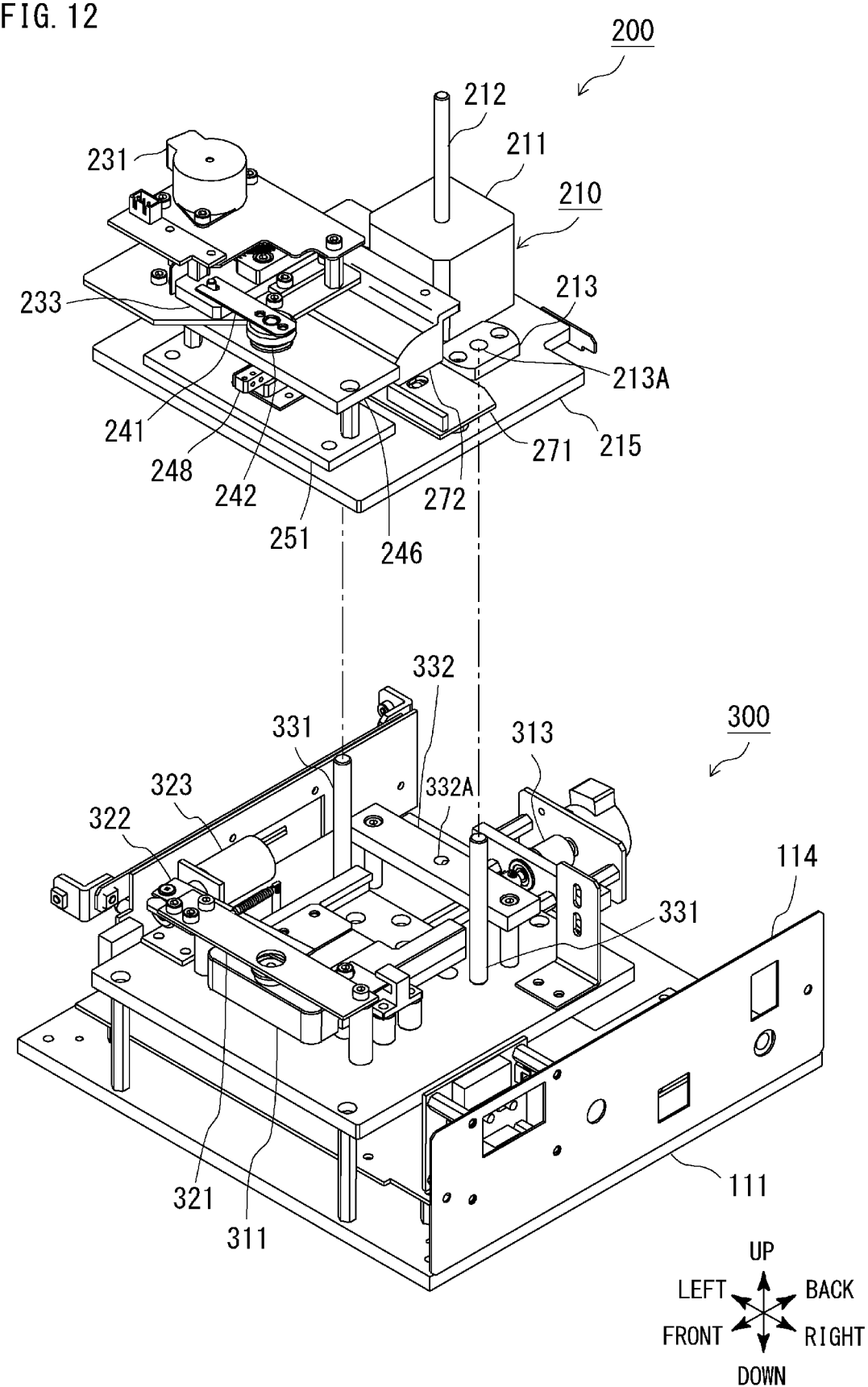
FIG. 12 is a perspective view when the upper unit is detached from the lower unit.
Figure 13:
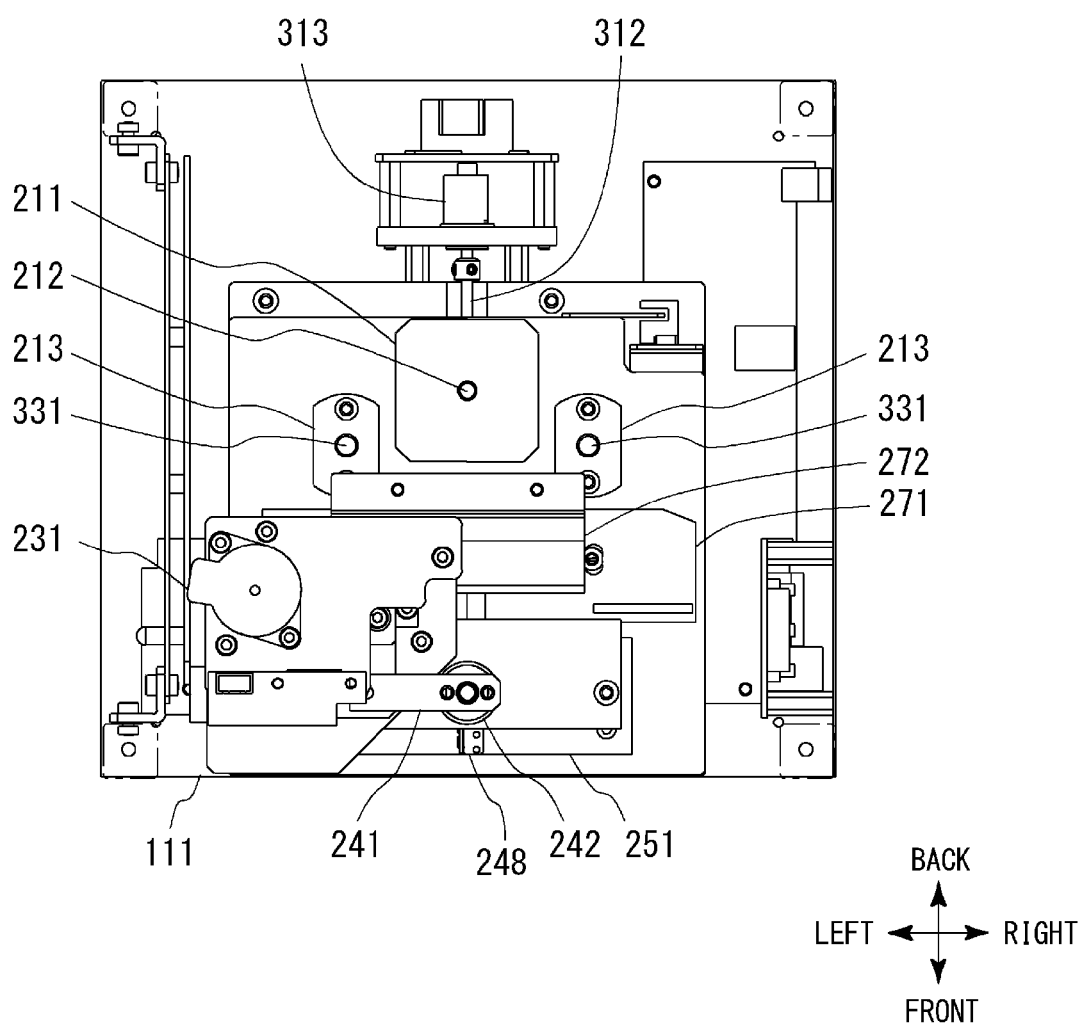
FIG. 13 is a plan view when the upper unit and the lower unit are assembled.

The following will describe coupling of the upper unit 200 and the lower unit 300 with reference to FIGS. 12 to 14. FIG. 12 is a perspective view when the upper unit 200 is detached from the lower unit 300. The support shafts 331 are disposed in the vertical direction on both sides of the edge on the back side of the placing table 311. The support shafts 331 support the upper unit 200 by being inserted in the support shaft guides 213 of the upper unit 200.

FIG. 13 is a plan view when the upper unit 200 and the lower unit 300 are assembled. The support shaft guides 213 are disposed at two positions on both sides of the lifting motor 211 in generally middle between the front face and back face of the blood coagulation test device 100. The upper unit 200 is supported by the support shafts 331 at two positions around the middle of the blood coagulation test device 100 in a plan view, and the upper unit 200 can be lifted or lowered by the lifting mechanism 210 in a stable manner.

Figure 14A:
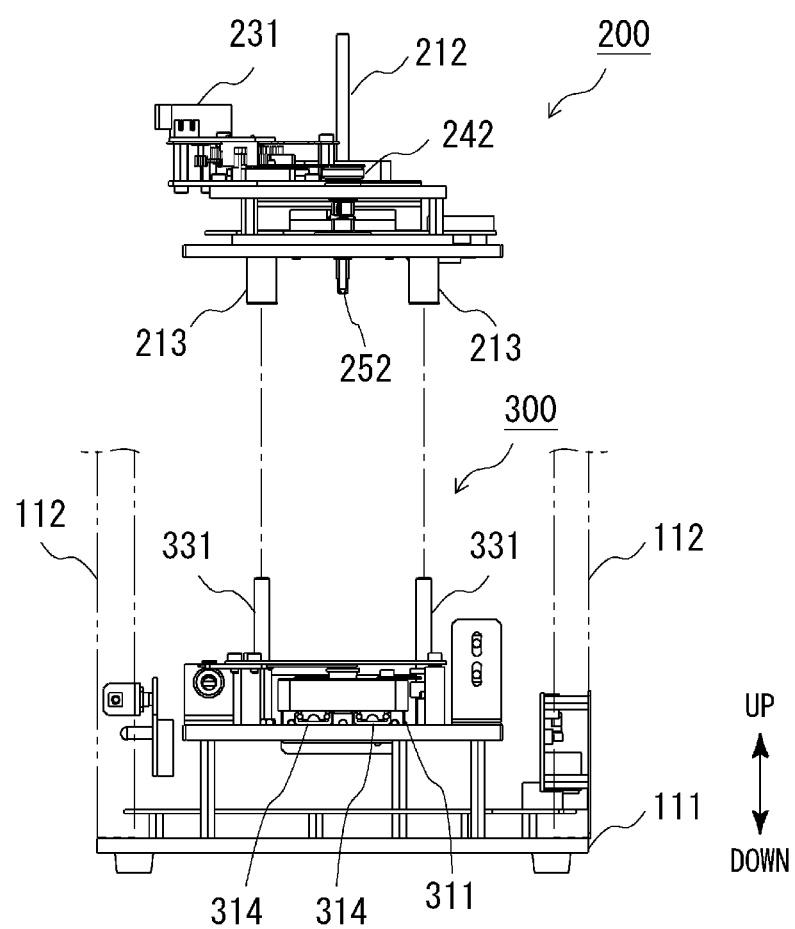
FIG. 14A is a left side view illustrating a state where the upper unit is detached from the lower unit.
Figure 14B:
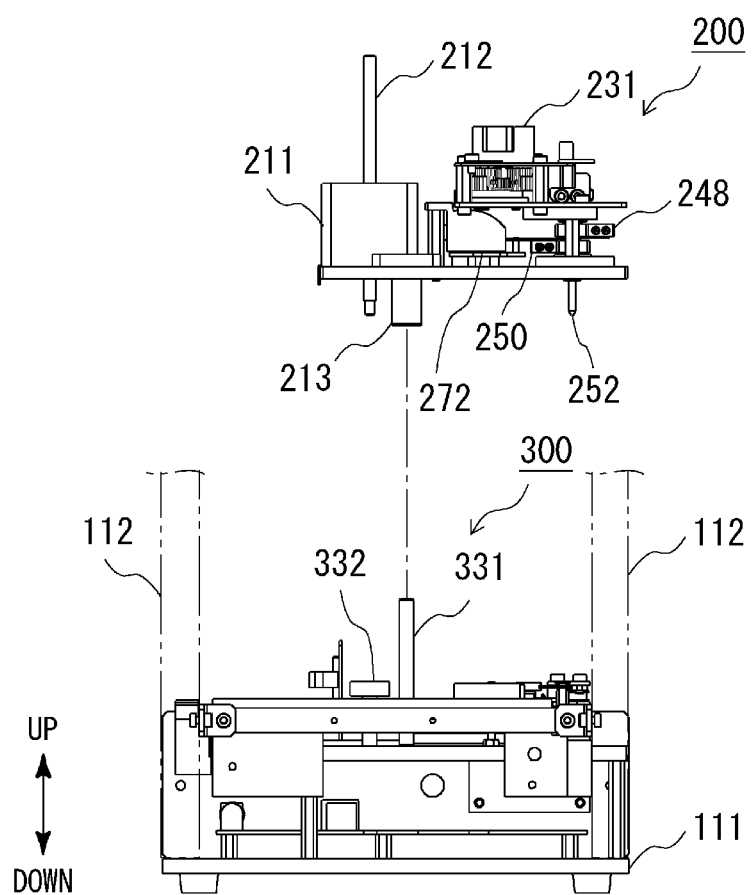
FIG. 14B is a front view illustrating a state where the upper unit is detached from the lower unit.

FIG. 14A is a left side view illustrating a state where the upper unit 200 is detached from the lower unit 300. FIG. 14B is a front view illustrating a state where the upper unit 200 is detached from the lower unit 300. As illustrated in FIG. 14A, the support shafts 331 of the lower unit 300 are inserted in the support shaft guides 213 of the upper unit 200. When the container 40 and the stirring part 30 are installed on the container installation part 311A of the placing table 311, lowering the upper unit 200 causes the holding pin 252 to be inserted in the holding pin insertion hole 30A provided on the top face of the stirring part 30. Note that, in FIG. 14B, when the upper unit 200 and the lower unit 300 are assembled, the lower end of the shaft 212 of the upper unit 200 is fitted and fixed in the fitting hole 332A provided in the upper unit support table 332.

Flow of Operation

FIG. 15 is a flowchart exemplifying the flow of the operation of the blood coagulation test device according to the second embodiment. Further, FIGS. 16A to 20B illustrate the operation of the lifting mechanism 210, stirring control mechanism 230, stirring motion transmission mechanism 240, rotation angle measurement mechanism 270, placing table slide mechanism 310, and holding pin pull-out mechanism 320, which respectively drive operations illustrated in FIG. 15. The flow of the operation illustrated in FIG. 15 starts when the blood coagulation test device 100 according to the second embodiment receives a test start command from the control device according to the second embodiment.

First, at step S201, the placing table slide mechanism 310 slides the placing table 311 forward to a position where the container 40 can be installed. The container 40 and the stirring part 30 housed in the container 40 are installed on the container installation part 311A of the placing table 311 that was slid forward. Once the container 40 and the stirring part 30 are installed, the placing table slide mechanism 310 slides the placing table 311 to the original position. Here, with reference to FIGS. 16A and 16B, the operation of the placing table by the placing table slide mechanism 310 will be described.

Figure 16A:
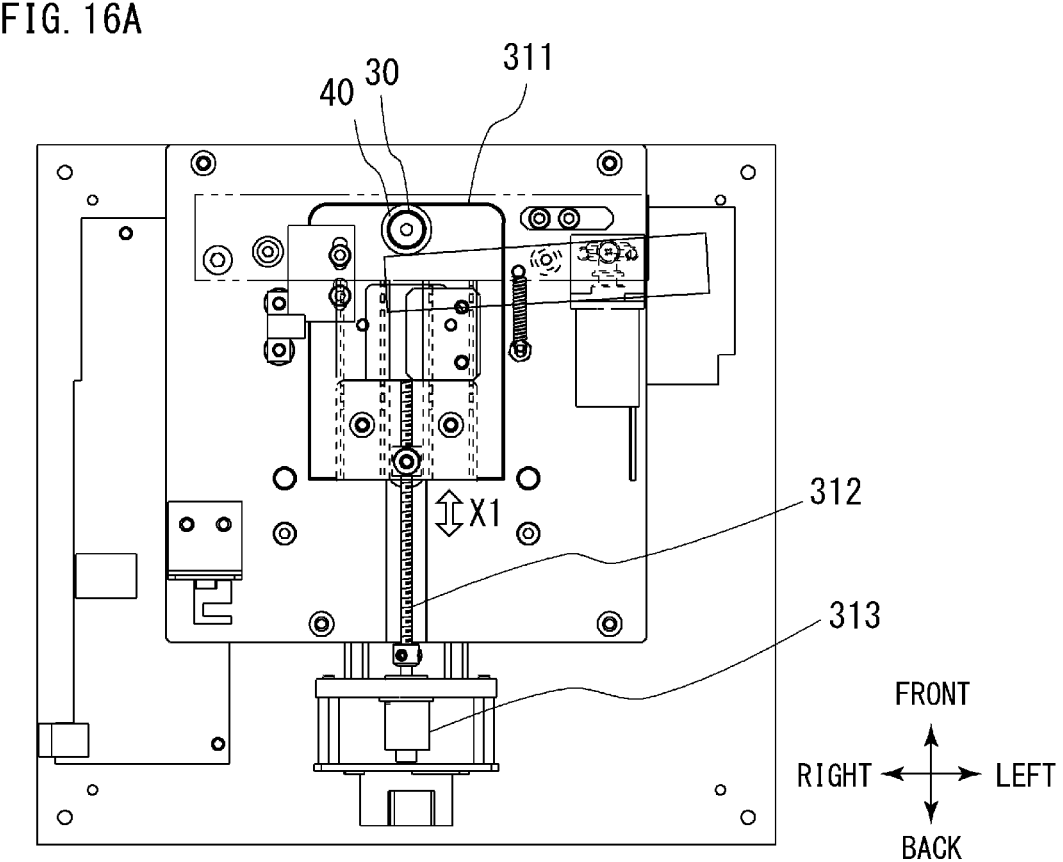
FIG. 16A is a diagram illustrating a state where a placing table is housed in the blood coagulation test device.

FIG. 16A is a diagram illustrating a state where the placing table 311 is housed in the blood coagulation test device 100. FIG. 16B is a diagram illustrating a state where the placing table 311 is slid forward and the container 40 can be installed on the placing table 311. The placing table 311 can slide in the direction of the arrow X1 illustrated in FIGS. 16A and 16B when the slide motor 313 drives the rotary motion of the ball screw 312. Note that the placing table 311 can linearly move by sliding along the linear guides 314. At step S201, the placing table slide mechanism 310 slides the placing table 311 forward to a position where the container 40 can be installed, as illustrated in FIG. 16B. When the container 40 and the stirring part 30 are installed, the placing table slide mechanism 310 slides the placing table 31 backward to a position illustrated in FIG. 16A so as to return it to the original position.

Next, at step S202, the lifting mechanism 210 lowers the upper unit 200 and inserts the holding pin 252 into the holding pin insertion hole 30A provided on top of the stirring part 30. Since the holding pin 252 has generally the same diameter as that of the holding pin insertion hole 30A, the holding pin 252 can hold the stirring part 30 by being inserted into the holding pin insertion hole 30A. Further, at step S203, as the lifting mechanism 210 lifts the upper unit 200, the stirring part 30 held by the holding pin 252 is taken out from the container 40. When the stirring part 30 is taken out from the container 40, a blood specimen can be injected in the container 40. The following will describe the lifting and lowering operation of the upper unit 200 by the lifting mechanism 210 with reference to FIGS. 17A and 17B.

Figure 17A:
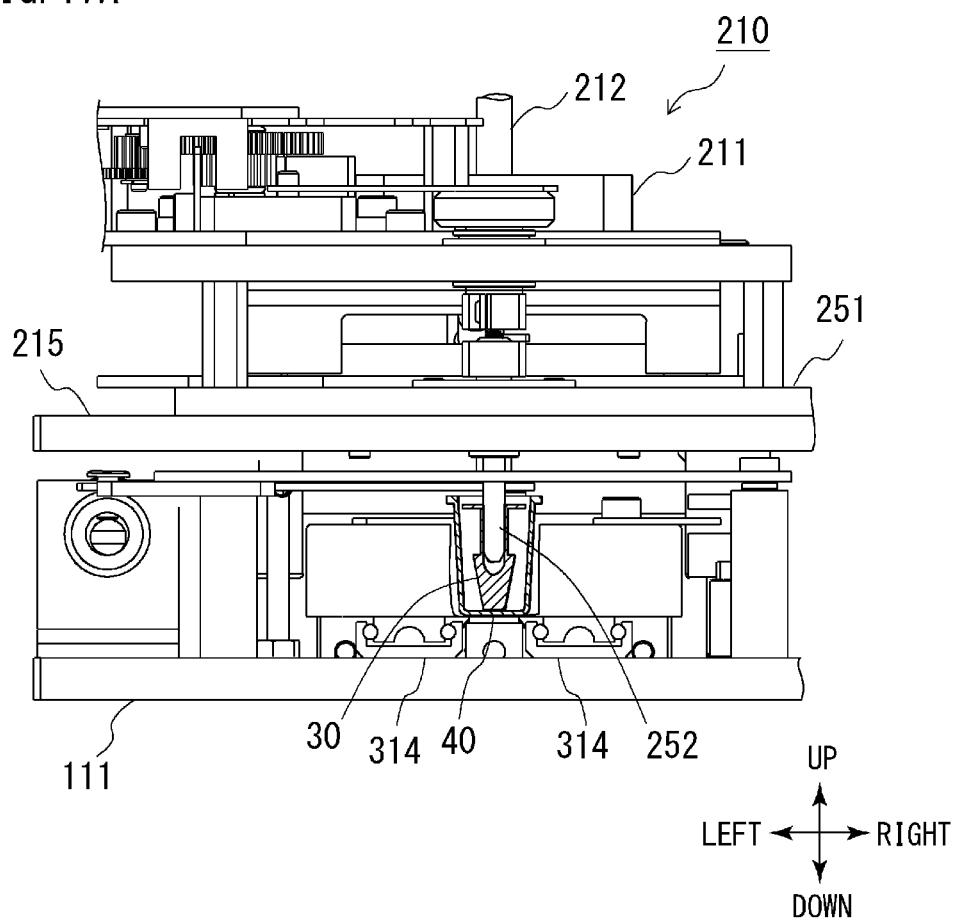
FIG. 17A is a diagram illustrating a state where lowering of the upper unit causes a holding pin to be inserted in a stirring part.
Figure 17B:
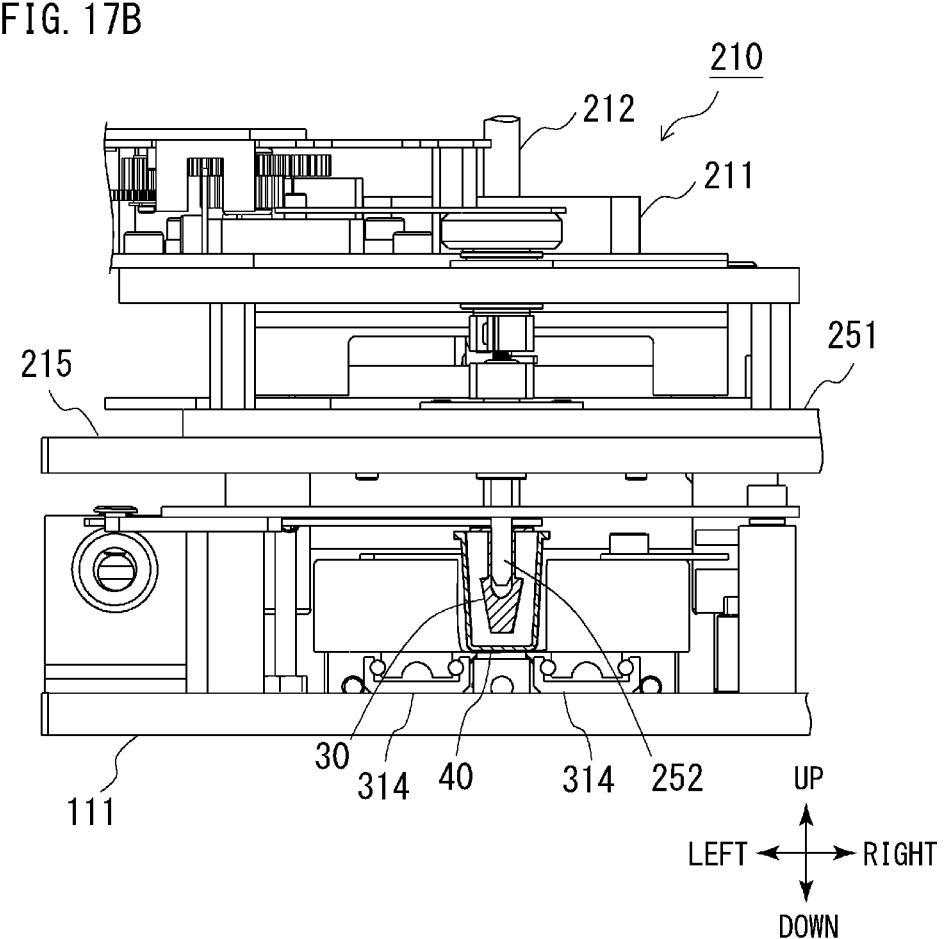
FIG. 17B is a diagram illustrating a state where the upper unit is lifted to a position where the stirring part can stir a blood specimen in the container.

FIG. 17A is a diagram illustrating a state where the holding pin 252 is inserted in the stirring part 30 by lowering the upper unit 200. FIG. 17B is a diagram illustrating a state where the upper unit 200 is lifted to a position where the stirring part 30 can stir the blood specimen in the container 40. The lifting mechanism 210 can lift or lower the upper unit 200 by rotating a female screw that is screwed in the shaft 212 provided in the lifting motor 211 by driving the lifting motor 211. The lifting mechanism 210 can lift or lower the upper unit 200 to a desired height. At step S202, the lifting mechanism 210 may lower the upper unit 200 until the holding pin 252 is inserted into the stirring part 30 to a depth where the holding pin 252 can hold the stirring part 30. At step S203, the lifting mechanism 210 further lifts the upper unit 200 higher than the state of FIG. 17B so as to lift the stirring part 30 to a height where a blood specimen can be injected into the container 40.

At step S204, the upper unit 200 is in a state where the upper unit 200 is lifted by the processing of step S203. The placing table slide mechanism 310 slides the placing table 311 forward again. The stirring part 30 in the container 40 was taken out by the holding pin 252 through the processing of step S202, and a blood specimen can be injected into the container 40. Once a blood specimen is injected in the container 40, the placing table slide mechanism 310 slides the placing table 311 backwards to the original position.

At step S205, the lifting mechanism 210 adjusts the height of the stirring part 30 so as to be able to stir the blood specimen in the container 40. For example, the lifting mechanism 210 may lower the upper unit 200 up to the height where the leading end of the stirring part 30 is not in contact with the bottom of the container 40 as illustrated in FIG. 17B.

At step S206, a blood coagulation test is performed. First, the stirring control mechanism 230 converts the rotary motion of the stirring motor 231 to the oscillatory motion of the oscillation plate 241. Next, the stirring motion transmission mechanism 240 transmits the oscillatory motion of the oscillation plate 241 to the oscillation receiving part 250.

The oscillation receiving part 250 further transmits the transmitted oscillatory motion to the holding pin 252. The stirring part 30 held by the holding pin 252 stirs the blood specimen in the container 40 by performing an oscillatory motion in conjunction with the holding pin 252. The rotation angle measurement mechanism 270 measures the rotation angle of the stirring part 30 and transmits the measurement result to the control device according to the second embodiment. The following will describe the stirring control mechanism 230, stirring motion transmission mechanism 240, and rotation angle measurement mechanism 270 with reference to FIGS. 18, 19A, 19B, and 19C.

Figure 18:
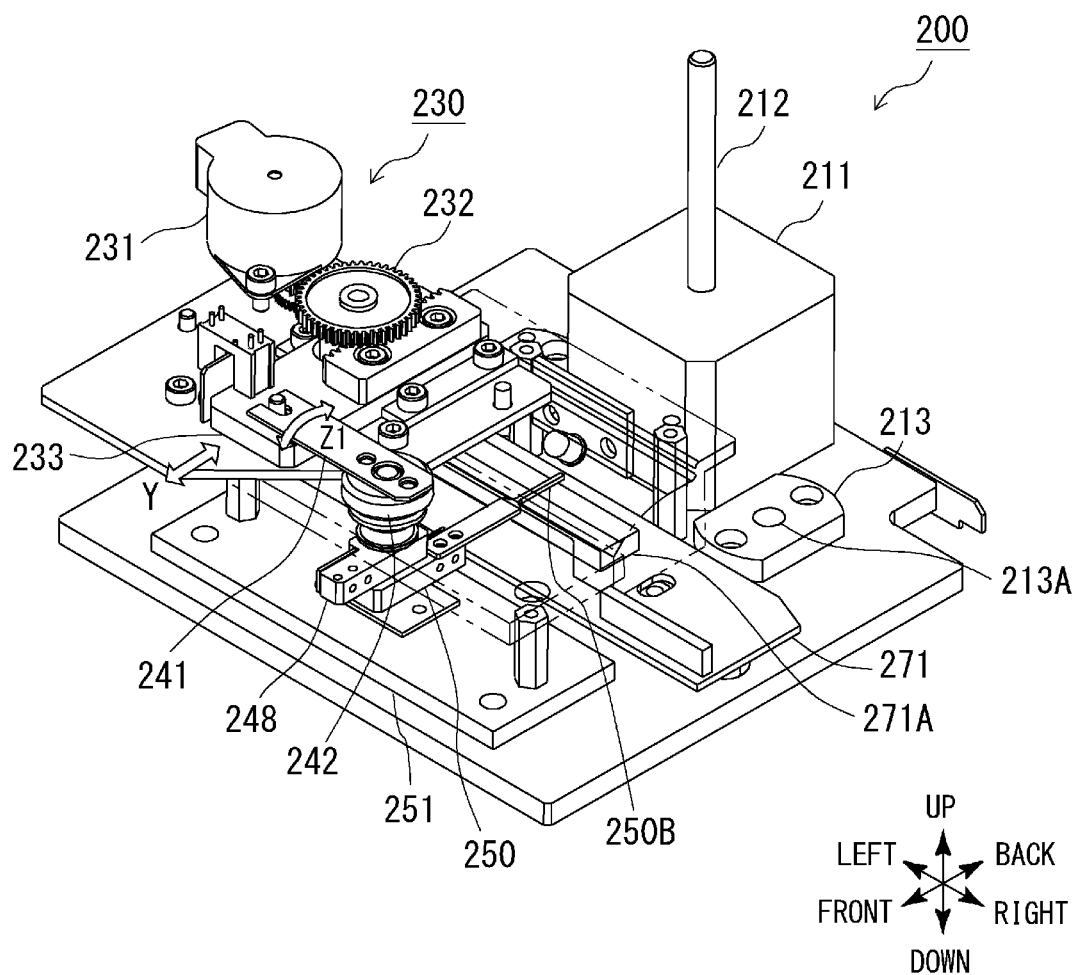
FIG. 18 is a diagram exemplifying the operation for converting a rotary motion of a gear into an oscillatory motion of an oscillation plate by a stirring control mechanism.

FIG. 18 is a diagram exemplifying an operation where the stirring control mechanism 230 converts the rotary motion of the gear 232 into the oscillatory motion of the oscillation plate 241. The stirring control mechanism 230 rotationally drives the gear 232 by the stirring motor 231. The rotary motion of the gear 232 is converted into the reciprocating movement in the arrow Y direction of the sliding plate 233. By controlling the rotation rate of the stirring motor 231, the amplitude of the reciprocating movement of the sliding plate 233 can be adjusted to a predetermined width. Further, by the reciprocating movement of the sliding plate 233, the oscillation plate 241 performs an oscillatory motion in the Z1 direction about the rotation axis 244 as a rotation axis.

Figure 19A:
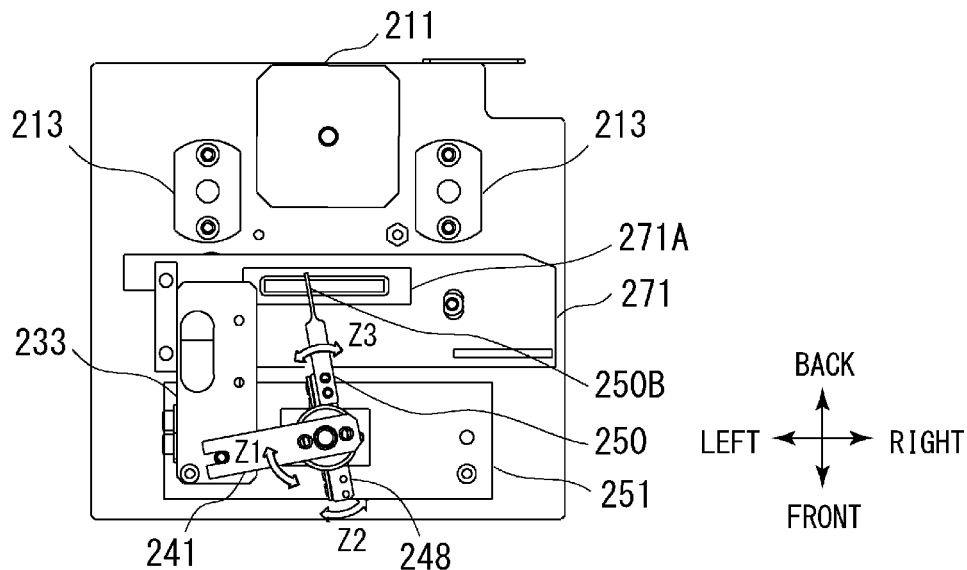
FIG. 19A is a diagram illustrating a rotational state of the oscillation plate when the sliding plate has moved to the front side.
Figure 19B:
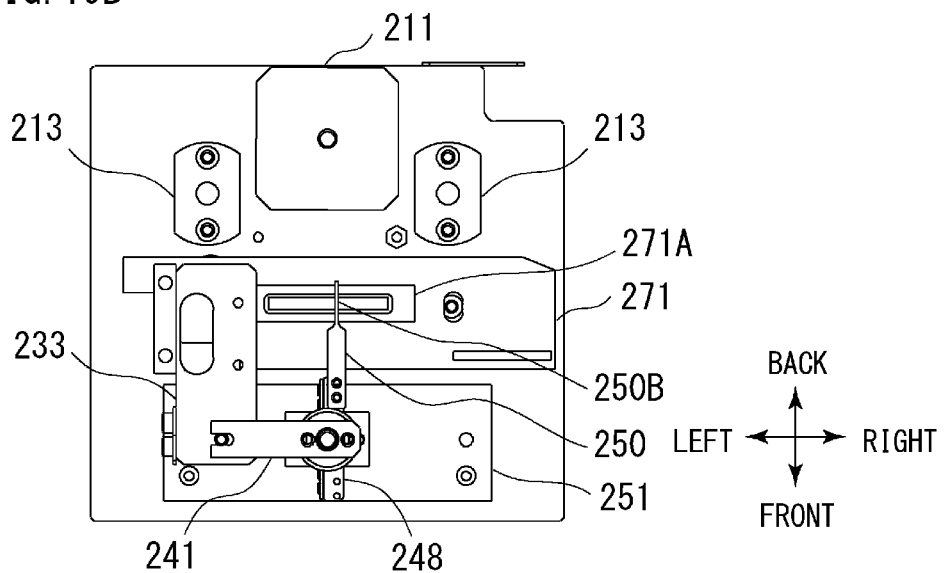
FIG. 19B is a diagram illustrating a rotational state of the oscillation plate when the sliding plate has not moved.
Figure 19C:
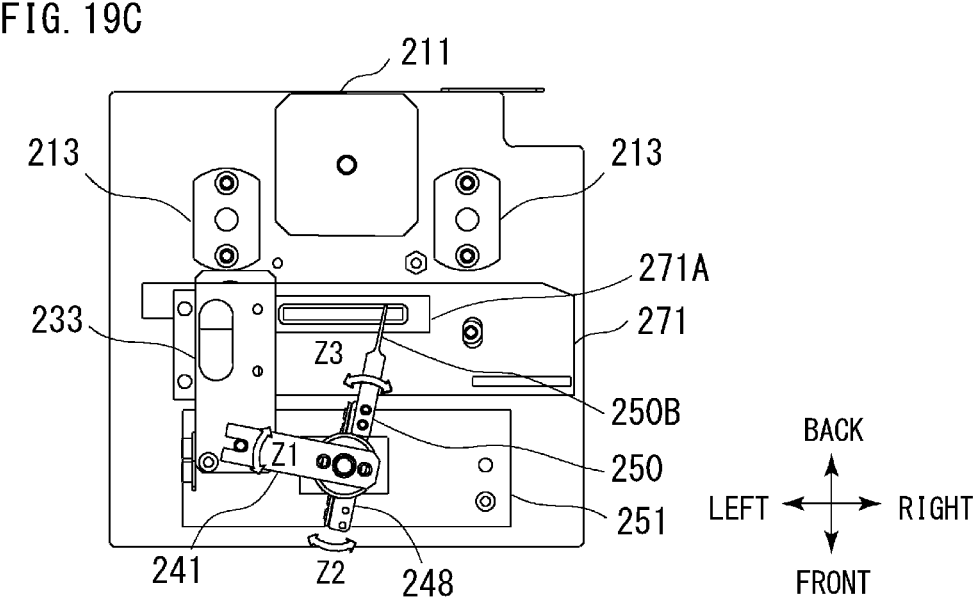
FIG. 19C is a diagram illustrating a rotational state of the oscillation plate when the sliding plate has moved to the back side.

FIGS. 19A to 19C exemplify the operation where the stirring motion transmission mechanism 240 transmits the oscillatory motion of the oscillation plate 241 to the oscillation receiving part 250. FIG. 19A is a diagram illustrating a rotational state of the oscillation plate 241 when the sliding plate 233 has moved to the front side. FIG. 19B is a diagram illustrating a rotational state of the oscillation plate 241 when the sliding plate 233 has not moved. FIG. 19C is a diagram illustrating a rotational state of the oscillation plate 241 when the sliding plate 233 has moved to the back side. The oscillation plate 241 repeats the states of FIGS. 19A and 19C, such as from FIG. 19A, FIG. 19B, FIG. 19C, FIG. 19B, FIG. 19A, FIG. 19B . . . , with the state of FIG. 19B as a reference point.

The stirring motion transmission mechanism 240 transmits the oscillatory motion in the Z1 direction of the oscillation plate 241 to the oscillation transmission part 248. The oscillation transmission part 248 coordinates with the oscillation plate 241 through the rotation axis 244 and performs the oscillatory motion in the Z2 direction about the rotation axis 244 as a rotation axis. The stirring motion transmission mechanism 240 transmits the oscillatory motion in the Z2 direction of the oscillation transmission part 248 to the oscillation receiving part 250 through the elastic body 249. The oscillation receiving part 250 performs an oscillatory motion in the Z3 direction about the holding pin 252 as a rotation axis.

The rotation angle measurement mechanism 270 detects the rotation angle of the oscillation measurement pin 250B on the leading end side of the oscillation receiving part 250 with the optical sensor 271A equipped on the sensor plate 271. The optical sensor 271A detects light irradiated from the above light source part 272 with linearly arranged light reception elements. The rotation angle measurement mechanism 270 can measure the rotation angle of the oscillation measurement pin 250B based on a position where light is not detected due to the movement of the oscillation measurement pin 250B. Since the oscillation measurement pin 250B oscillates in conjunction with the holding pin 252, if the rotation angle of the holding pin 252 reduces due to coagulation of blood in the container 40, the rotation angle of the oscillation measurement pin 250B decreases as well. Thus, the rotation angle measurement mechanism 270 can measure the rotation angle of the holding pin 252 (and the stirring part 30 held by the holding pin 252) by measuring the rotation angle of the oscillation measurement pin 250B.

At step S207, after the test has ended, the holding pin pull-out mechanism 320 pulls out the holding pin 252 from the stirring part 30. The holding pin pull-out mechanism 320 can pull out the holding pin 252 from the stirring part 30 by the lifting mechanism 210, that is, by lifting the lifting mechanism 210 while pressing the top of the stirring part 30. The following will describe the operation where the holding pin pull-out mechanism 320 pulls out the holding pin 252 from the stirring part 30 with reference to FIGS. 20A and 20B. It is assumed that, in FIG. 20A, the holding pin 252 is inserted in the holding pin insertion hole 30A of the stirring part 30.

Figure 20A:
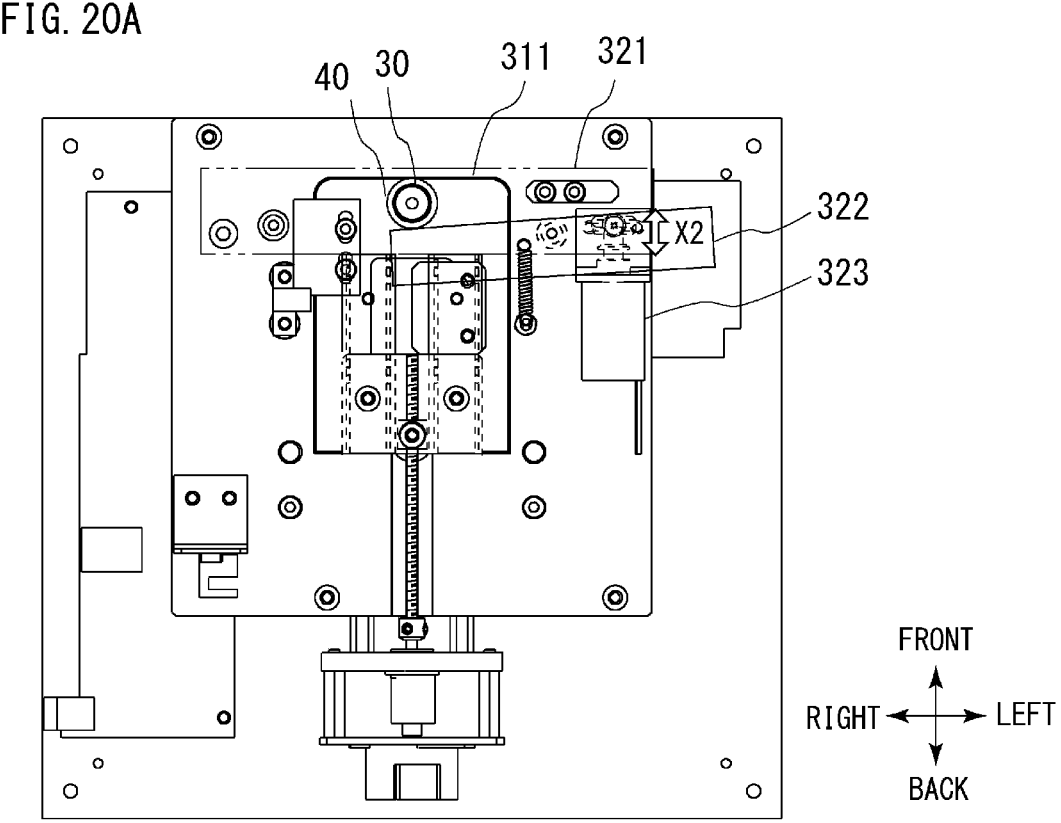
FIG. 20A is a diagram illustrating a state where a holding plate does not hold the stirring part.
Figure 20B:
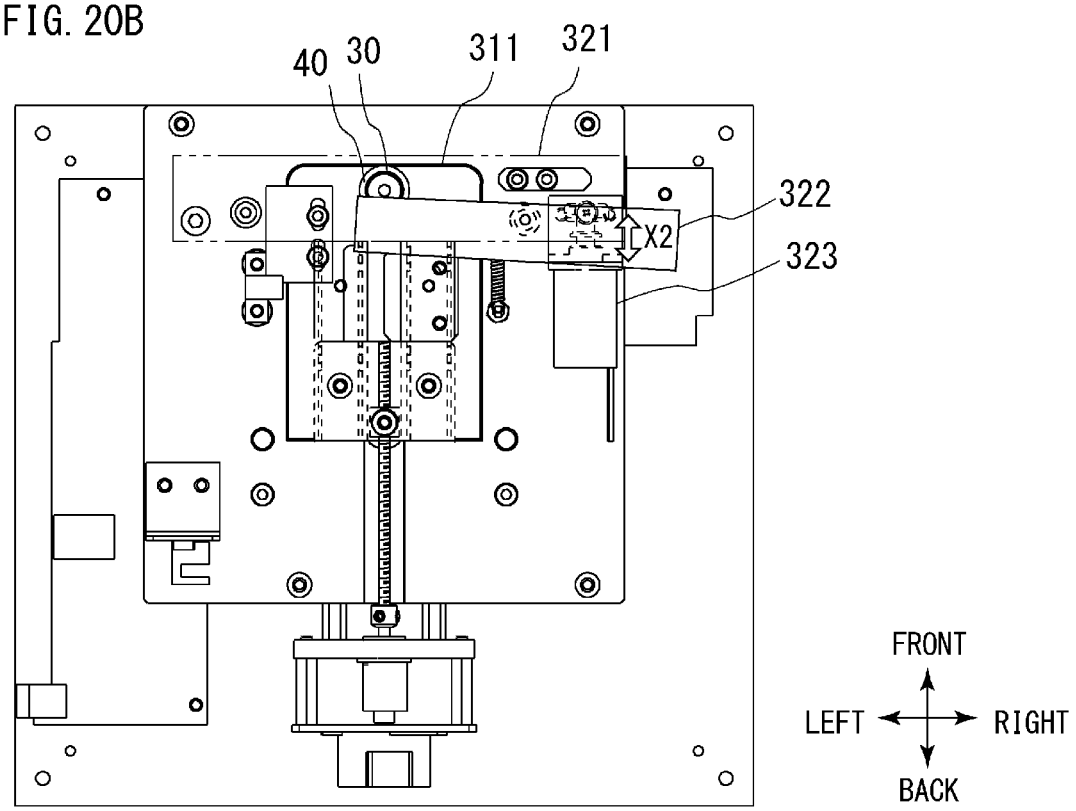
FIG. 20B is a diagram illustrating a state where the holding plate holds the stirring part when the holding pin is pulled out from the stirring part.

FIG. 20A is a diagram illustrating a state where the holding plate 322 does not hold the stirring part 30. FIG. 20B is a diagram illustrating a state where the holding plate 322 holds the stirring part 30 when the holding pin 252 is pulled out from the stirring part 30. By energizing and de-energizing the solenoid 323, the holding plate 322 receives a force in the arrow X2 direction and changes the angle to respectively the state of FIG. 20B and the state of FIG. 20A.

In the state of FIG. 20A, the holding plate 322 does not overlap the container 40 and the stirring part 30 in a plan view. As such, the holding plate 322 is not in contact with the container 40 and the stirring part 30. Thus, the stirring part 30 held by the holding pin 252 is lifted together with the upper unit 200 by the lifting mechanism 210. Whereas, in the state of FIG. 20B, the holding plate 322 overlaps the top surface of the stirring part 30 in a plan view. Since the holding plate 322 holds the upper part of the stirring part 30 held by the holding pin 252, when the upper unit 200 is lifted by the lifting mechanism 210, the holding pin 252 is pulled out from the stirring part 30.

According to the blood coagulation test device 100 of the second embodiment, by controlling the rotation rate of the stirring motor 231, the rotation rate and rotation angle transmitted to the stirring part 30 can be appropriately controlled. Thus, a resolution according to a test object can be obtained by the test with the blood coagulation test device 100. In addition, the blood coagulation test device 100 includes operation mechanisms, such as a lifting mechanism 210, a placing table slide mechanism 310, and a holding pin pull-out mechanism 320, thereby promoting automation and simplification of a blood coagulation test.

Examples According to Second Embodiment

The following will describe examples according to the second embodiment to describe the present invention more specifically. However, the present invention is not limited to the following Examples.

In the second embodiment, Examples where a spring with higher sensitivity (that is, a finer/weaker spring) that is appropriate to measurement of a low viscoelastic area is selected as an elastic body 2 will be described. When highly viscoelastic area is measured, measurement is programmed by controlling the rotation rate of the motor and widening the rotation (amplitude) angle of the stirring part that stirs a blood specimen, whereby measurement in a wide range of viscoelasticity areas is made possible. For example, a method of analyzing the blood viscoelasticity by thromboelastometry and measuring the fibrinogen amount of blood in the presence of an anti-platelet agent has been disclosed (Cited document 1: US20090130645 "Method for assessing the fibrinogen contribution in coagulation"). Gel (clot) that is constituted only by fibrin in the presence of an anti-platelet agent has lower viscoelasticity than gel (clot) that is constituted by both activated platelets and fibrin in normal blood. As such, gel constituted only by fibrin in the presence of an anti-platelet agent is suitable for measurement using a thinner/weaker spring in a range of approximately ±4 to 10 degrees.

If a highly viscoelastic area is analyzed in a condition of a spring and amplitude angle that have the same high sensitivity as for measuring a low viscoelastic area, a sufficient resolution and accuracy cannot be obtained for the highly viscoelastic area. That is, the movement of the oscillation measurement pin may stop before the blood coagulates and reaches the maximum viscoelasticity. To prevent such a situation, for example, in measurement of a highly viscoelastic area in a case of a hypercoagulable state (with increased fibrinogen), thrombocytosis, or the like, the rotation angle of an oscillatory motion to be transmitted to the stirring part is widening to ±5 degrees or more, preferably to ±10 to 20 degrees. In this way, a strong force can be applied to the oscillation measurement pin through the spring, and highly accurate measurement of the highly viscoelastic area is made possible even with a spring with high sensitivity. Further, even in a blood coagulant test of high viscoelasticity, the initial rotation angle of the stirring part may be set to 4 to 10 degrees and, after observing a decrease in the amplitude due to the start of blood coagulation, the rotation angle may be widened to 10 to 20 degrees. In such a case, even if the rotation angle is widened to 10 to 20 degrees, since blood viscoelasticity has already started to rise, the rotation angle of the stirring part can be suppressed to approximately 5 degrees, thus, the gel structure of blood coagulation can be prevented from being destroyed by the large amplitude of the stirring part. If a weaker spring that does not destroy gel is used, fibrin gel is not destroyed even with the rotation angle of ±10 degrees or more. However, when a weaker spring is used, the rotation angle is required to be further widened for analysis of high viscoelasticity. The rotation angle of the stirring part is selected according to the sensitivity of a spring and the shapes of the spring and the stirring part. In this way, when a device (system) is configured to use a highly sensitive spring catering to measurement of a low viscoelastic area, and the same device is used for measuring a highly viscoelastic area by controlling the rotation rate of the motor and changing (widening) the rotation angle of the oscillatory motion transmitted to the spring and the stirring part, assay (analysis, evaluation) of a variety of viscoelastic areas can be performed with high sensitivity. As exemplified in the following examples 3 to 11, the rotation angle of the oscillatory motion transmitted to the spring and stirring part can be changed for each purpose of measurement according to the state of viscoelasticity or the like of a test-object blood (including plasma).

Example 3

Example 3 is an example of analyzing a normal blood specimen of high viscoelasticity. First, venous blood was collected in a blood collection tube containing 3.2% sodium citrate. Ten µL of ten-fold diluted PT reagent (r-PT, Hemos IL RecombiPlasTin, IL Japan Co., Ltd.), 20 µL of 0.2 M calcium chloride, and 300 µL of blood were placed in the container 40. The container 40 was kept at a temperature of 37° C. and, by controlling the stirring motor 231, the oscillation transmission part 248 was oscillated in a range of ±4.8 degrees. The oscillation of the oscillation transmission part 248 was transmitted to the stirring part 30 through the elastic body 249, the oscillation receiving part 250, and the holding pin 252. Two types of helical torsion coil springs were used as the elastic body 249.

Figure 21:
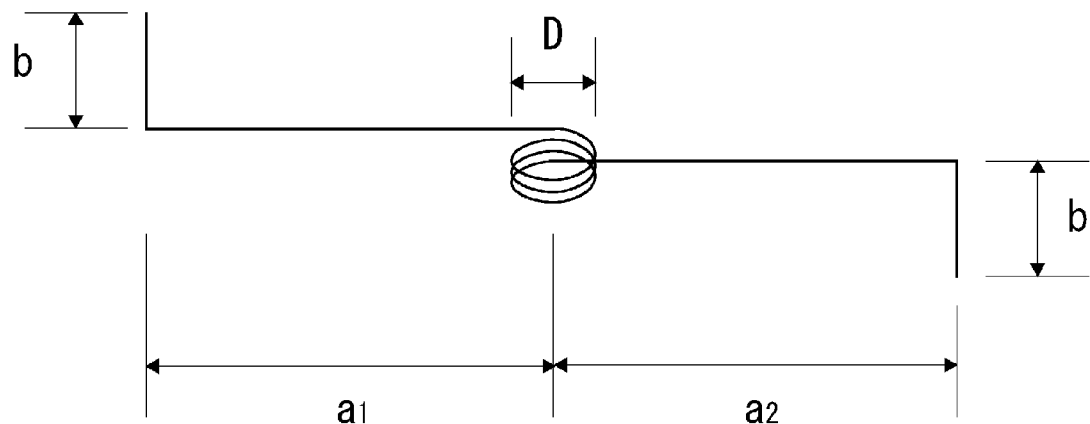
FIG. 21 is a diagram exemplifying a helical torsion coil spring used in an example of a second embodiment.

FIG. 21 exemplifies the helical torsion coil spring used in the Examples of the second embodiment. When the wire diameter of the helical torsion coil spring is defined as dmm and the number of turns of the coil is n, in the Examples of the second embodiment, a helical torsion coil spring of arm length $a_1$=15 mm, arm length $a_2$=15 mm, arm length b=5 mm, center diameter D=2 mm, wire diameter d=0.16 mm, and the number of turns n=2 was used as a spring A. Further, a helical torsion coil spring of arm length $a_1$=10 mm, arm length $a_2$=10 mm, arm length b=3 mm, center diameter D=2 mm, wire diameter d=0.12 mm, and the number of turns=2 was used as a second spring B. The spring constants kTd of the spring A and the spring B were respectively calculated as 0.0044 Nmm/deg and 0.0017 Nmm/deg from the following equation (Math. 1):

$$kTd = \frac{E \times d^4}{3667 \times D \times n + 389 \times (a_1 + a_2)} \qquad [\text{Math. 1}]$$

E: Longitudinal elastic modulus (SUS, Steel special Use Stainless)=$186 \times 10^3$ N/mm$^2$ Even when a wire spring is used, the spring constant kTd can be changed by changing the wire diameter d and arm lengths $a_1$ and $a_2$. When a helical torsion coil spring is used, as indicated in (Math. 1), the spring constant kTd can be more flexibly changed by further changing the center diameter D and the number of turns n.

In Example 3, one reciprocation of the amplitude of the oscillation transmission part 248 that was controlled by the stirring motor 231 was set to 5.2 seconds, and the oscillation transmission part 248 was set to stop for 1 second at both ends. That is, the actual oscillation time of the oscillation transmission part 248 was 3.2 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation.

Figure 22:
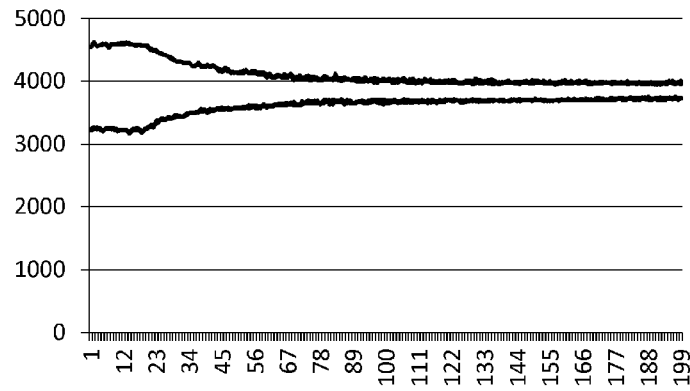
FIG. 22 is a graph illustrating measurement results when a spring A is used in Example 3.

FIG. 22 is a graph illustrating measurement results when the spring A was used in Example 3. The vertical axis indicates the position of the oscillation measurement pin 250B and the horizontal axis indicates the amplitude number. In the graph of FIG. 22, when the spring A was used, a distance from a predetermined reference position was measured for four times for each end of each amplitude of the oscillation measurement pin 250B and the average value of the distances of the four times was plotted.

Figure 23:
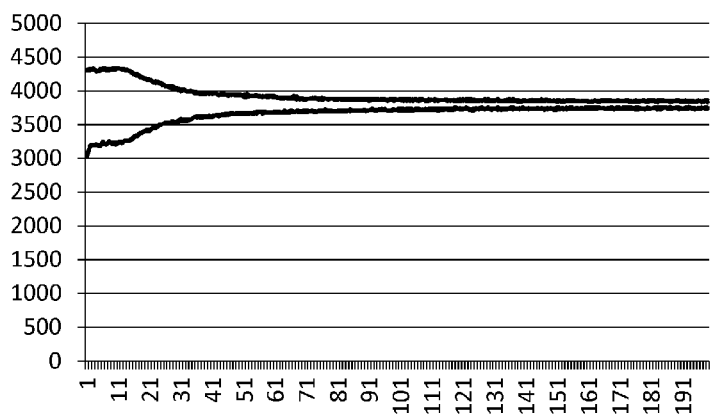
FIG. 23 is a graph illustrating measurement results when a spring B is used in Example 3.

FIG. 23 is a graph illustrating measurement results when the spring B was used in Example 3. The vertical axis and the horizontal axis are the same as those of FIG. 22. In the graph of FIG. 23, when the spring B was used, a distance from a predetermined reference position was measured for four times for each end of each amplitude of the oscillation measurement pin 250B and the average value of the distances of the four times was plotted.

Figure 24:
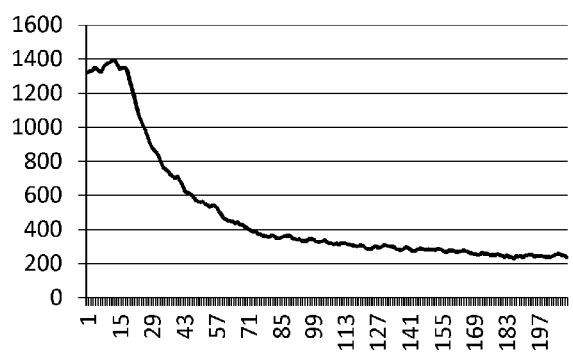
FIG. 24 is a graph illustrating amplitudes when the spring A is used in Example 3.

FIG. 24 is a graph illustrating amplitudes when the spring A was used in Example 3. The vertical axis indicates the amplitude of the oscillation measurement pin 250B and the horizontal axis indicates the amplitude number. The amplitude of the oscillation measurement pin 250B is a difference of positions at both ends of the oscillation measurement pin 250B as illustrated in FIG. 22. Note that the graph of FIG. 24 is sequential plotting of the average value of three amplitudes to level the graph.

Figure 25:
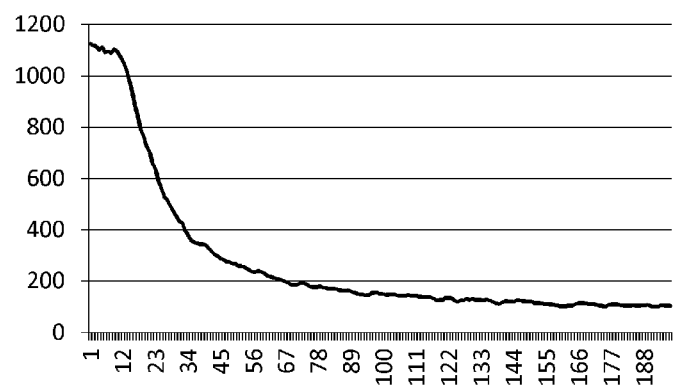
FIG. 25 is a graph illustrating amplitudes when the spring B is used in Example 3.

FIG. 25 is a graph illustrating amplitudes when the spring B is used in Example 3. The vertical axis and the horizontal axis are the same as FIG. 24. The amplitude of the oscillation measurement pin 250B is a difference of positions at both ends of the oscillation measurement pin 250B as illustrated in FIG. 23. Note that the graph of FIG. 25 is sequential plotting of the average value of three amplitudes in the same way as FIG. 24.

The changes of viscoelasticity due to blood coagulation can be detected with both spring A and spring B. However, it became apparent that, while the oscillation measurement pin 250B is almost in halt in the process of blood coagulation with the spring B as illustrated in FIG. 23, the oscillation measurement pin 250B maintains a certain rotation even after the blood coagulation has completed with the spring A as illustrated in FIG. 22. It also became apparent that, when measuring the amplitude of the oscillation measurement pin 250B and analyzing blood coagulation by oscillating the oscillation transmission part 248 within the range of ±4.8 degrees by the stirring motor 231, the spring A has higher sensitivity for accurately measuring changes in viscoelasticity of blood in a highly viscoelastic area than spring B.

Example 4

Example 4 is an example where a blood specimen of low viscoelasticity constituted only by fibrin gel in the presence of an anti-platelet agent is analyzed. Venous blood was collected in a blood collection tube containing 3.2% sodium citrate. Fifteen μL of APTT reagent (Sysmex Corporation), 20 μL of Fibtem reagent (Tem innovations Gmbh, containing cytochalasin D and calcium chloride), and 300 μL of blood are placed in the container 40. The container 40 was kept at a temperature of 37° C. and, by controlling the stirring motor 231, the oscillation transmission part 248 was oscillated in a range of ±4.8 degrees. The oscillation of the oscillation transmission part 248 is transmitted to the stirring part 30 through the elastic body 249, the oscillation receiving part 250, and the holding pin 252. The string A and string B were used as the elastic body 249 in the same way as Example 3.

In Example 4, one reciprocation of the amplitude of the oscillation transmission part 248 that was controlled by the stirring motor 231 was set to 5.2 seconds, and the oscillation transmission part 248 was set to stop for 1 second at both ends. That is, the actual oscillation time of the oscillation transmission part 248 was 3.2 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation.

Figure 26:
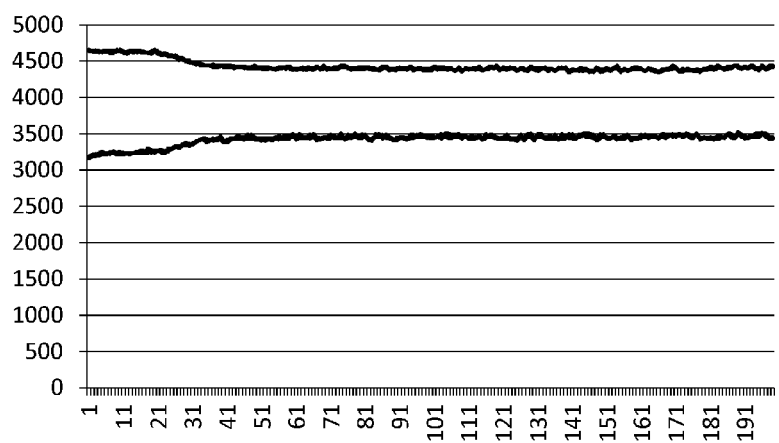
FIG. 26 is a graph illustrating measurement results when the spring A is used in Example 4.

FIG. 26 is a graph illustrating measurement results when the spring A was used in Example 4. The vertical axis indicates the position of the oscillation measurement pin 250B and the horizontal axis indicates the amplitude number. In the graph of FIG. 26, when the spring A was used, a distance from a predetermined reference position was measured for four times for each end of each amplitude of the oscillation measurement pin 250B and the average value of the distances of the four times was plotted.

Figure 27:
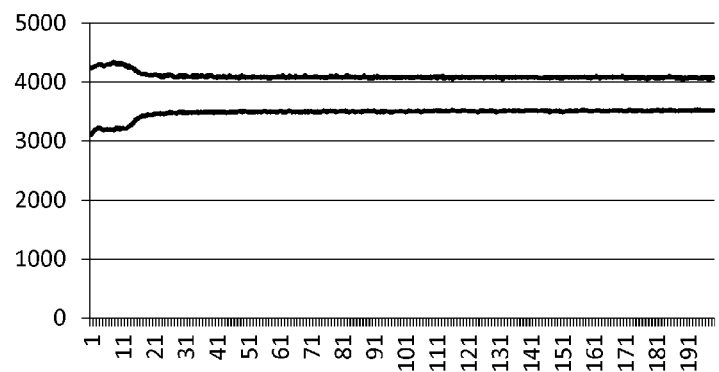
FIG. 27 is a graph illustrating measurement results when the spring B is used in Example 4.

FIG. 27 is a graph illustrating measurement results when the spring B was used in Example 4. The vertical axis and the horizontal axis are the same as FIG. 26. In the graph of FIG. 27, when the spring B was used, a distance from a predetermined reference position was measured for four times for each end of each amplitude of the oscillation measurement pin 250B and the average value of the distances of the four times was plotted.

Figure 28:
FIG. 28 is a graph illustrating amplitudes when the spring A is used in Example 4.

FIG. 28 is a graph illustrating amplitudes when the spring A was used in Example 4. The vertical axis indicates the amplitude of the oscillation measurement pin 250B and the horizontal axis indicates the amplitude number. The amplitude of the oscillation measurement pin 250B is a difference of positions at both ends of the oscillation measurement pin 250B as illustrated in FIG. 26. Note that the graph of FIG. 28 is sequential plotting of the average value of three amplitudes to level the graph.

Figure 29:
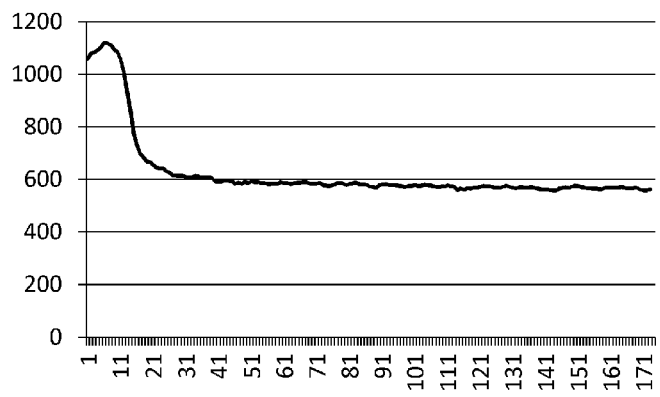
FIG. 29 is a graph illustrating amplitudes when the spring B is used in Example 4.

FIG. 29 is a graph illustrating amplitudes when the spring B was used in Example 4. The vertical axis and the horizontal axis are the same as FIG. 28. The amplitude of the oscillation measurement pin 250B is a difference of positions at both ends of the oscillation measurement pin 250B as illustrated in FIG. 27. Note that the graph of FIG. 29 is sequential plotting of the average value of three amplitudes in the same way as FIG. 28.

To assess viscoelasticity caused by fibrin clot while suppressing the platelet function, measurement should be sensitive for a change in a low viscoelastic area than measurement in a coagulation test using normal blood specimen. When the spring B is used, the amplitude (rotation angle) of the oscillation measurement pin 250B changes according to the change in viscoelasticity due to blood coagulation, and sensitive and stable data can be obtained with regard to the change (amplitude width) in viscoelasticity. On the other hand, when the spring A is used, a change in amplitude (rotation angle) of the oscillation measurement pin 250B is limited, the sensitivity is lower than that of the spring B, and the obtained data forms an unstable waveform.

Example 5

Example 5 is an example of analyzing a blood specimen that is diluted or added with fibrinogen. Venous blood was collected in a blood collection tube containing 3.2% sodium citrate. Fifteen μL of APTT reagent, 20 μL of Fibtem reagent, 300 μL of blood were placed in the container 40. The container 40 was kept at a temperature of 37° C. and, by controlling the stirring motor 231, the oscillation transmission part 248 was oscillated in a range of ±4.8 degrees. The oscillation of the oscillation transmission part 248 is transmitted to the stirring part 30 through the elastic body 249, the oscillation receiving part 250, and the holding pin 252. The string B was used as the elastic body 249.

In Example 5, one reciprocation of the amplitude of the oscillation transmission part 248 that was controlled by the stirring motor 231 was set to 5.2 seconds and the oscillation transmission part 248 was set to stop for 1 second at both ends. That is, the actual oscillation time of the oscillation transmission part 248 was 3.2 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation. Further, the same measurement was performed for a blood sample that was diluted to 50% with saline solution and a blood sample that was diluted to 50% with saline solution and added with 1 mg/mL of fibrinogen.

Figure 30:
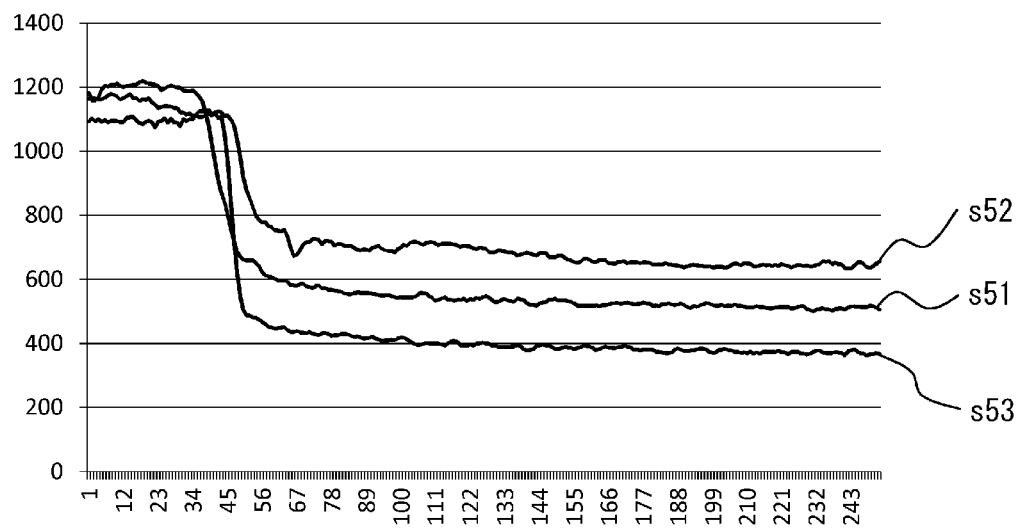
FIG. 30 is a graph illustrating amplitudes of an oscillation measurement pin in Example 5.

FIG. 30 is a graph illustrating amplitudes of the oscillation measurement pin in Example 5. The vertical axis indicates the amplitude of the oscillation measurement pin 250B and the horizontal axis indicates the amplitude number. The amplitude of the oscillation measurement pin 250B is a difference between the average values of positions measured for four times on both ends of the amplitude of the oscillation measurement pin 250B. FIG. 30 is sequential plotting of the average value of three amplitudes. The graph s51 indicates changes in amplitude obtained from the measurement results of a blood specimen in the presence of an anti-platelet agent. The graph s52 indicates changes in amplitude obtained from the measurement results of a sample of a blood specimen that was diluted to 50% with saline solution. The graph s53 indicates changes in amplitude obtained from the measurement results of a sample of blood that was diluted to 50% with saline solution and added with 1 mg/mL of fibrinogen. Using the spring B that is thinner than the spring A, a change in viscoelasticity, with regard to blood coagulation viscoelasticity, due to blood dilution or addition of fibrinogen while suppressing the platelet function can be measured with high sensitivity.

Example 6

Example 6 is an example of analyzing a blood specimen when the rotation angle of the oscillation transmission part 248 varies. Venous blood was collected in a blood collection tube containing 3.2% sodium citrate. Fifteen μL of APTT reagent, 20 μL of 0.2 M calcium chloride, 300 μL of blood were placed in the container 40. The container 40 was kept at a temperature of 37° C. and, by controlling the stirring motor 231, the oscillation transmission part 248 was oscillated in ranges of ±4.8 degrees and ±10.4 degrees. The oscillation of the oscillation transmission part 248 is transmitted to the stirring part 30 through the elastic body 249, the oscillation receiving part 250, and the holding pin 252. The string B was used as the elastic body 249.

In Example 6, one reciprocation of the amplitude of the oscillation transmission part 248 that was controlled by the stirring motor 231 was set to 5.2 seconds when the rotation range was ±4.8 degrees, 7.7 seconds when the rotation range was ±10.4 degrees, and, in both cases, the oscillation transmission part 248 was set to stop for 1 second at both ends. That is, the actual oscillation time of the oscillation transmission part 248 was respectively 3.2 seconds and 5.7 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation.

Figure 31:
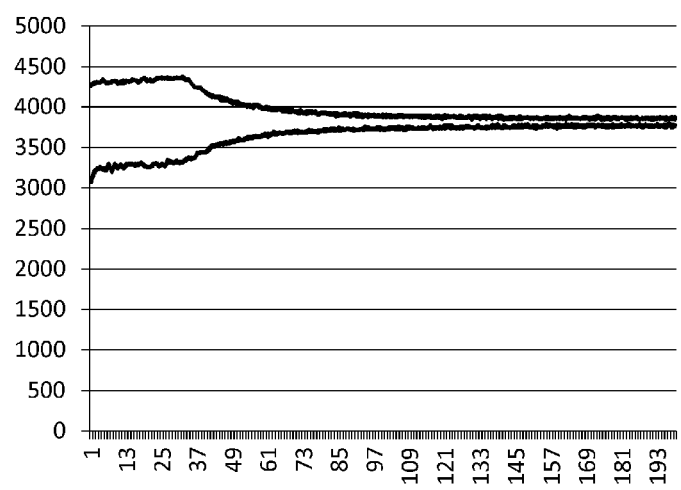
FIG. 31 is a graph illustrating measurement results of oscillation in a range of ±4.8 degrees in Example 6.

FIG. 31 is a graph illustrating measurement results of oscillation in the range of ±4.8 in Example 6. The vertical axis indicates the position of the oscillation measurement pin 250B and the horizontal axis indicates the amplitude number. In the graph of FIG. 31, when the oscillation transmission part 248 was oscillated in the range of ±4.8 degrees using the spring B, distances, from a predetermined reference position, which were measured on both ends of each amplitude of the oscillation measurement pin 250B were plotted.

Figure 32:
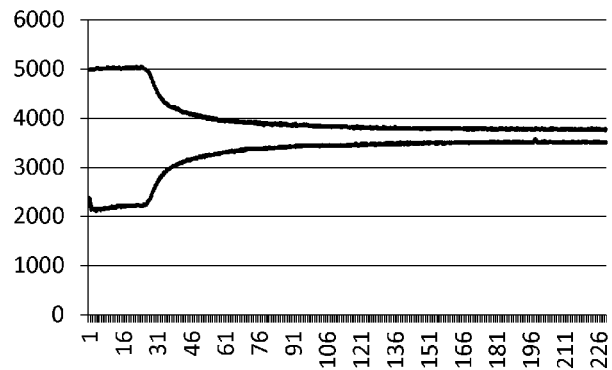
FIG. 32 is a graph illustrating measurement results of oscillation in a range of ±10.4 degrees in Example 6.

FIG. 32 is a graph illustrating measurement results of oscillation in the range of ±10.4 degrees in Example 6. The vertical axis indicates the position of the oscillation measurement pin 250B and the horizontal axis indicates the amplitude number. In the graph of FIG. 32, when the oscillation transmission part 248 was oscillated in the range of ±10.4 degrees using the spring B, distances, from a predetermined reference position, which were measured on both ends of each amplitude of the oscillation measurement pin 250B were plotted.

When the oscillation transmission part 248 was oscillated in the range of ±4.8 degrees, the oscillation measurement pin 250B nearly stopped at the end of blood coagulation. Whereas, when the oscillation transmission part 248 is oscillated in the range of ±10.4 degrees, the oscillation measurement pin 250B maintained the oscillating state even after blood coagulation. It became apparent that, by widening the rotation angle of the oscillation transmission part 248, a stronger force is applied to the oscillation measurement pin 250B and, as the result, a change in viscoelasticity due to blood coagulation in a highly viscoelastic area can be more sensitively analyzed even when the spring B (a weak spring with high sensitivity in a low viscoelastic area) is used.

Example 7

Example 7 is an example where, after blood coagulation has started, analysis is performed with increased rotation angle of the oscillation transmission part 248. Venous blood was collected in a blood collection tube containing 3.2% sodium citrate. Twenty μL of APTT reagent, 20 μL of 0.2 M calcium chloride, and 300 μL of blood were placed in the container 40. The container 40 was kept at a temperature of 37° C. and, by controlling the stirring motor 231, the oscillation transmission part 248 was oscillated in a range of ±4.8 degrees. The oscillation of the oscillation transmission part 248 is transmitted to the stirring part 30 through the elastic body 249, the oscillation receiving part 250, and the holding pin 252. The string B was used as the elastic body 249.

In Example 7, one reciprocation of the amplitude of the oscillation transmission part 248 that is controlled by the stirring motor 231 was set to 5.2 seconds, and the oscillation transmission part 248 was set to stop for 1 second at both ends. That is, the actual oscillation time of the oscillation transmission part 248 is 3.2 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation.

After the measurement has started, a decrease in amplitude of the oscillation measurement pin 250B due to blood coagulation was detected and the rotation angle of the oscillation transmission part 248 was increased to ±10.4 degrees and the analysis was continued. After the increase of the rotation angle of the oscillation transmission part 248, the one reciprocation of amplitude of the oscillation transmission part 248 was set to 7.7 seconds and the oscillation transmission part 248 was set to stop for 1 second at both ends. That is, the actual oscillation time of the oscillation transmission part 248 was 5.7 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation.

Figure 33:
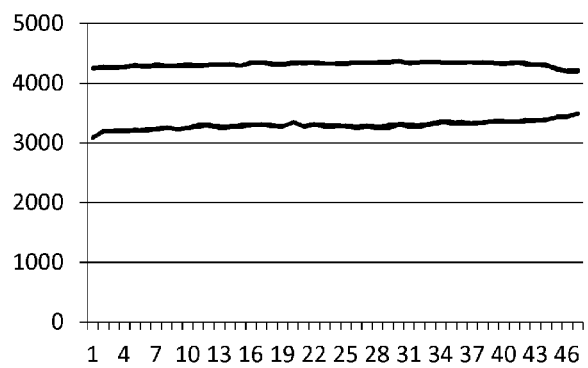
FIG. 33 is a graph of measurement results before increasing the rotation angle of an oscillation transmission part in Example 7.

FIG. 33 is a graph of measurement results before increasing the rotation angle of the oscillation transmission part in Example 7. The vertical axis indicates the position of the oscillation measurement pin 250B and the horizontal axis indicates the amplitude number. In the graph of FIG. 33, after the start of measurement, when the oscillation transmission part 248 was oscillated in the range of ±4.8 degrees, distances, from a predetermined reference position, which were measured on both ends of each amplitude of the oscillation measurement pin 250B were plotted.

Figure 34:
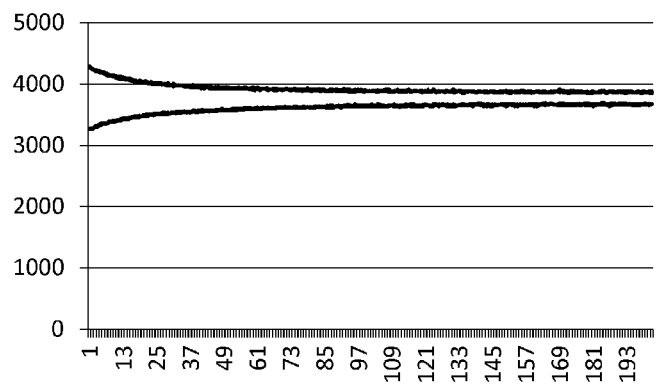
FIG. 34 is a graph of measurement results after increasing the rotation angle of the oscillation transmission part in Example 7.

FIG. 34 is a graph of measurement results after the rotation angle of the oscillation transmission part was increased in Example 7. The vertical axis indicates the position of the oscillation measurement pin 250B, and the horizontal axis indicates the amplitude number after increasing the rotation angle of the oscillation transmission part 248. In the graph of FIG. 34, when the rotation angle of the oscillation transmission part 248 was increased and the oscillation transmission part 248 was oscillated in the range of ±10.4 degrees, distances, from a predetermined reference position, which were measured on both ends of each amplitude of the oscillation measurement pin 250B were plotted.

In analysis of viscoelasticity due to blood coagulation using the spring B, viscoelasticity of normal blood can be analyzed in a condition where the real amplitude of the oscillation measurement pin 250B was suppressed within a certain range, by increasing the rotation angle of the oscillation transmission part 248 by control of the stirring motor 231 only after detecting a decrease in the amplitude of the oscillation measurement pin 250B due to the increase of viscoelasticity of the blood specimen. When measuring a highly viscoelastic area using a thinner spring (with lower spring constant) than the spring A, the rotation angle is required to be widened to larger than 5 degrees, with a possibility of destroying a blood coagulant clot (gel). In such a case, by increasing the rotation angle of the oscillation transmission part 248 after the viscoelasticity of blood has been increased with the start of the blood coagulation, the real amplitude of the oscillation measurement pin 250B can be suppressed to a certain range of angle, which is considered effective in suppressing destroying of gel.

Example 8

Example 8 is an example of analyzing viscoelasticity of plasma. Further, in Example 8, plasma added with a thrombolytic agent was also analyzed. After venous blood was collected in a blood collecting tube containing 3.2% sodium citrate, plasma was obtained by centrifugation. Fifteen µL of APTT reagent, 20 µL of 0.2 M calcium chloride, 300 µL of blood were placed in the container 40. The container 40 was kept at a temperature of 37° C. and, by controlling the stirring motor 231, the oscillation transmission part 248 was oscillated in a range of ±5.8 degrees. The oscillation of the oscillation transmission part 248 is transmitted to the stirring part 30 through the elastic body 249, the oscillation receiving part 250, and the holding pin 252. The string B was used as the elastic body 249.

In Example 8, one reciprocation of the amplitude of the oscillation transmission part 248 that was controlled by the stirring motor 231 was set to 5.6 seconds, and the oscillation transmission part 248 was set to stop for 1 second at both ends. That is, the actual oscillation time of the oscillation transmission part 248 was 3.6 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation. Further, 150, 300, and 600 IU of t-PA was added to the plasma and the same measurement was performed.

Figure 35:
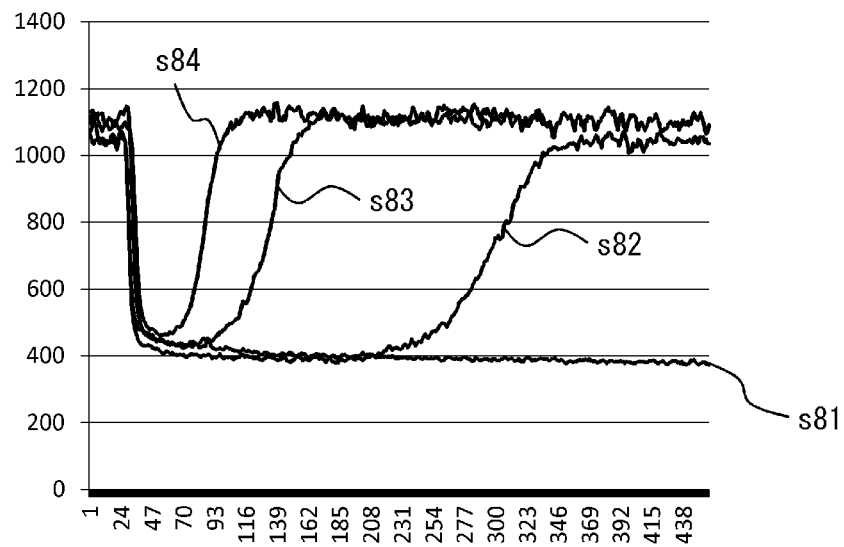
FIG. 35 is a graph illustrating amplitudes of the oscillation measurement pin in Example 8.

FIG. 35 is a graph illustrating amplitudes of the oscillation measurement pin in Example 8. The vertical axis indicates the amplitude of the oscillation measurement pin 250B and the horizontal axis indicates the amplitude number. The amplitude of the oscillation measurement pin 250B is a difference between the average values of positions measured for four times on both ends of the amplitude of the oscillation measurement pin 250B. Each graph of FIG. 35 is sequential plotting of average values of three amplitudes. The graph s81 indicates changes in amplitude obtained from the measurement results of plasma. The graph s82 indicates changes in amplitude obtained from the measurement results of a plasma sample added with 150 IU of t-PA. The graph s83 indicates changes in amplitude obtained from the measurement results of a plasma sample added with 300 IU of t-PA. The graph s84 indicates changes in amplitude obtained from the measurement results of a plasma sample added with 600 IU of t-PA. It became apparent that fibrinolysis reaction when t-PA is added to plasma can be more sensitively measured using a weaker spring B than the spring A.

Example 9

Example 9 is an example of analyzing plasma that is diluted or added with fibrinogen. After venous blood was collected in a blood collecting tube containing 3.2% sodium citrate, plasma was obtained by centrifugation. Fifteen µL of APTT reagent, 20 µL of 0.2 M calcium chloride, and 300 µL of plasma were placed in the container 40. The container 40 was kept at a temperature of 37° C. and, by controlling the stirring motor 231, the oscillation transmission part 248 was oscillated in a range of ±4.8 degrees. The oscillation of the oscillation transmission part 248 is transmitted to the stirring part 30 through the elastic body 249, the oscillation receiving part 250, and the holding pin 252. The string B was used as the elastic body 249.

In Example 9, one reciprocation of the amplitude of the oscillation transmission part 248 that was controlled by the stirring motor 231 was set to 5 seconds and the oscillation transmission part 248 was set to stop for 1 second at both ends. That is, the actual oscillation time of the oscillation transmission part 248 was 3 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation. Further, the same measurement was performed for a plasma sample diluted to 50% with saline solution and a plasma sample diluted to 50% with saline solution and added with 1 mg/mL of fibrinogen.

Figure 36:
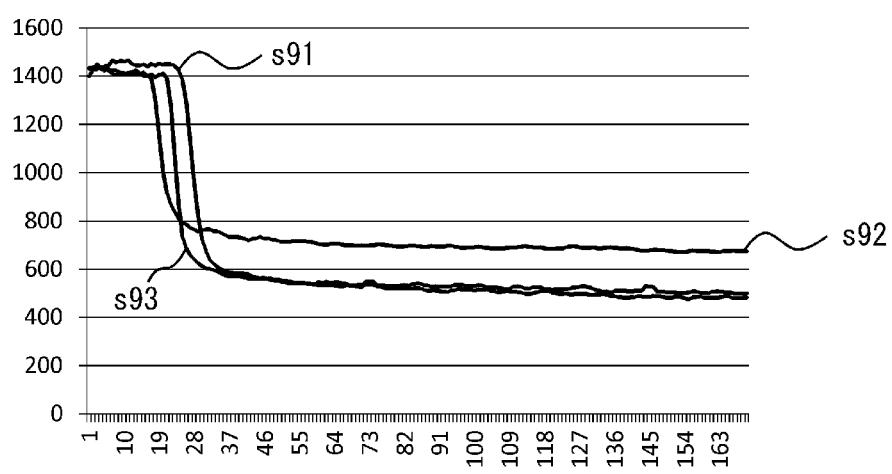
FIG. 36 is a graph illustrating amplitudes of the oscillation measurement pin in Example 9.

FIG. 36 is a graph illustrating amplitudes of the oscillation measurement pin in Example 9. The vertical axis indicates the amplitude of the oscillation measurement pin 250B and the horizontal axis indicates the amplitude number. The amplitude of the oscillation measurement pin 250B is a difference between the average values of positions measured for four times on both ends of the amplitude of the oscillation measurement pin 250B. Each graph of FIG. 36 is sequential plotting of the average value of three amplitudes. The graph s91 indicates changes in amplitude obtained from the measurement results of normal plasma. The graph s92 indicates changes in amplitude obtained from the measurement results of a plasma sample that was diluted to 50% with saline solution. The graph s93 indicates changes in amplitude obtained from the measurement results of a plasma sample that was diluted to 50% with saline solution and added with 1 mg/mL fibrinogen. With spring B that is thinner than spring A, a change in viscoelasticity caused by dilution of plasma or addition of fibrinogen can be measured with high sensitivity.

Example 10

Example 10 is an example of analyzing a hemolysis sample. Venous blood was collected in a blood collecting tube containing 3.2% sodium citrate, and was frozen and thawed to hemolyze the blood. Fifteen μL of APTT reagent, 20 μL of Fibtem reagent, 300 μL of hemolysate were placed in the container 40. The container 40 was kept at a temperature of 37° C. and, by controlling the stirring motor 231, the oscillation transmission part 248 was oscillated in a range of ±4.8 degrees. The oscillation of the oscillation transmission part 248 is transmitted to the stirring part 30 through the elastic body 249, the oscillation receiving part 250, and the holding pin 252. The string B was used as the elastic body 249.

In Example 10, one reciprocation of amplitude of the oscillation transmission part 248 that was controlled by the stirring motor 231 was set to 5 seconds and the oscillation transmission part 248 was set to stop for 1 second at both ends. That is, the actual oscillation time of the oscillation transmission part 248 was 3 seconds. The rotation angle of the stirring part 30 can be calculated from the amplitude of the oscillation measurement pin 250B provided at the leading end of the oscillation receiving part 250. The amplitude of the oscillation measurement pin 250B was obtained by measuring the position of the oscillation measurement pin 250B above the optical sensor 271A for four times with an interval of approximately 0.1 seconds starting from 0.4 seconds after the rotation of the oscillation transmission part 248 stops at each end and calculating the average value of the four times at each end of the rotation. Further, the same measurement was performed for a hemolysate sample diluted to 50% with saline solution and added with 1 mg/mL of fibrinogen.

Figure 37:
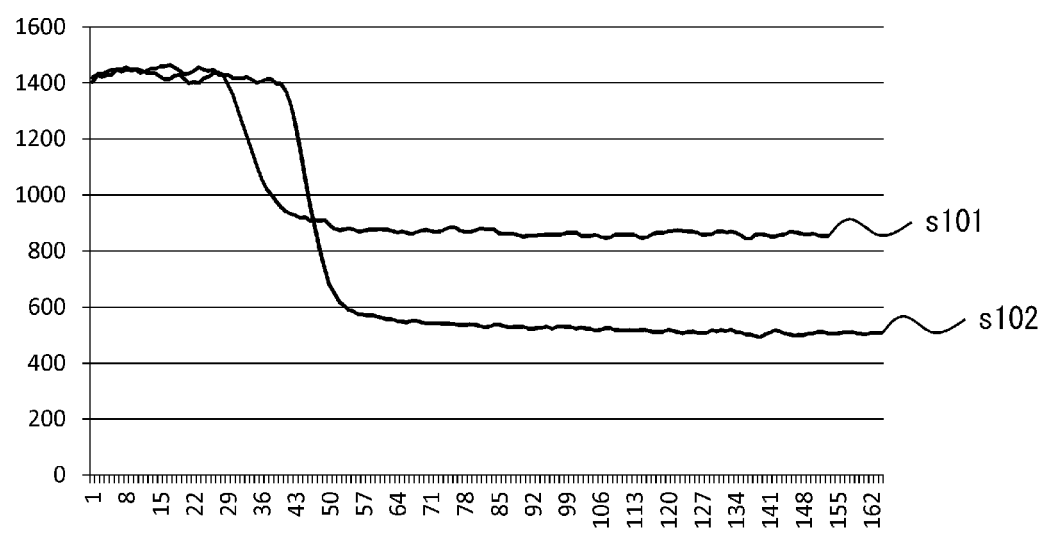
FIG. 37 is a graph illustrating amplitudes of the oscillation measurement pin in Example 10.

FIG. 37 is a graph illustrating amplitudes of the oscillation measurement pin in Example 10. The vertical axis indicates the amplitude of the oscillation measurement pin 250B and the horizontal axis indicates the amplitude number. The amplitude of the oscillation measurement pin 250B is a difference between the average values of positions measured for four times on both ends of the amplitude of the oscillation measurement pin 250B. Each graph of FIG. 37 is sequential plotting of the average value of three amplitudes. The graph s101 indicates changes in amplitude obtained from the measurement results of a hemolysate sample in the presence of an anti-platelet agent. The graph s102 indicates changes in amplitude obtained from the measurement results of a hemolysate sample that was diluted to 50% with saline solution and added with 1 mg/mL fibrinogen.

The change in blood viscoelasticity due to blood coagulation using hemolysate in the presence of an anti-platelet agent can be analyzed. Although analysis of blood viscoelasticity in the presence of an anti-platelet agent is used for analysis of the amount of fibrinogen, it has been reported that the increase/decrease of hematocrit affects correlation between blood viscoelasticity and fibrinogen amount in blood (cited literature 2: Anesth Analg. 2012 July; 115(1): 16-21; The impact of hematocrit on fibrin clot formation assessed by rotational thromboelastometry.) It became apparent that, using a hemolysate sample, measurement can be performed without being affected by hematocrit.

REFERENCE SIGNS LIST

10 Blood coagulation test device
1 Control unit
1A Servo motor
1B Elastic body support part
1C Elastic body support shaft
2 Elastic body
3 Stirring part
3A Rotation transmission part
3B Bearing
3C Stirring pin
3D Pinhole
4 Container
5 Sensor
6 Control device
11 CPU
12 RAM
13 ROM
14 Auxiliary storage device
15 NIC
16 Imaging unit
17 Display unit
18 Input unit
30 Stirring part 30A Holding pin insertion hole
30B Flange
40 Container
100 Blood coagulation test device
110 Case
111 Bottom plate
112 Support pillar
113 Panel
114 Connection panel
200 Upper unit
210 Lifting mechanism
211 Lifting motor
212 Shaft
213 Support shaft guide
215 Upper unit bottom plate
230 Stirring control mechanism
231 Stirring motor
232 Gear
233 Sliding plate
240 Stirring motion transmission mechanism
241 Oscillation plate
242 Rotator
243, 246A, 246B Washer
244 Rotation axis
245A, 245B Bearing
247 First base
248 Oscillation transmission part
249 Elastic body
250 Oscillation receiving part
250A Elastic body coupling part
250B Oscillation measurement pin
251 Second base
252 Holding pin
270 Rotation angle measurement mechanism
271 Sensor plate
272 Light source part
300 Lower unit
310 Placing table slide mechanism
311 Placing table
311A Container installation part
312 Ball screw
313 Slide motor
314 Linear guide
320 Holding pin pull-out mechanism
321 Guide plate
322 Holding plate
323 Solenoid
331 Support shaft
332 Upper unit support table

What is claimed is:

1. A blood coagulation test device comprising:
a container into which a test-object blood is placed;
a stirring part for stirring the test-object blood in the container;
an elastic body being connected to the stirring part at a position separated by a predetermined diameter from an axis of the stirring part and capable of deforming in response to a force received through stirring of the test-object blood from the stirring part;
a control unit for transmitting a predetermined rotary motion to the stirring part and causing the stirring part to rotate in a reciprocating manner in a circumferential direction by rotating the elastic body in a reciprocating manner about the axis of the stirring part as a rotational axis and controlling the reciprocating rotation at a position separated by a predetermined diameter from the rotational axis; and
a measurement unit for measuring a rotation angle pertaining to the reciprocating rotation of the stirring part.

2. The blood coagulation test device according to claim 1, wherein the control unit changes the predetermined reciprocating rotary motion according to the rotation angle measured by the measurement unit.

3. The blood coagulation test device according to claim 1, wherein the predetermined reciprocating rotary motion is a reciprocating rotary motion in a circumferential direction within a certain range of angle.

4. The blood coagulation test device according to claim 1, wherein the control unit controls the predetermined reciprocating rotary motion in such a way that the rotation angle of the stirring part becomes constant.

5. The blood coagulation test device according to claim 1, wherein the measurement unit corrects the rotation angle when the test-object blood is stirred using the elastic body, based on a difference between a first rotation angle that is measured by the measurement unit when a predetermined solution is stirred using the elastic body and a second rotation angle that is measured by the measurement unit when the predetermined solution is stirred using a reference elastic body as a reference for the elastic body.

6. The blood coagulation test device according to claim 5, wherein the predetermined solution is any of agarose or gelatin solution.

7. The blood coagulation test device according to claim 1, wherein the control unit changes the rotation angle of the predetermined reciprocating rotary motion that is transmitted to the stirring part, according to viscoelasticity of the test-object blood.

8. The blood coagulation test device according to claim 1, wherein the control unit widens the rotation angle of the predetermined reciprocating rotary motion that is transmitted to the stirring part after viscoelasticity of the test-object blood has started to increase.

9. The blood coagulation test device according to claim 1, wherein the measurement unit includes a measurement mechanism in which a light source irradiates a member to be measured that rotates in a reciprocating manner in conjunction with the stirring part above an optical sensor, and the optical sensor detects light from the light source.

10. The blood coagulation test device according to claim 1, further comprising: a detachment mechanism in which a press-holding member presses to hold a flange provided in a circumferential direction on the stirring part that is held by a holding member that transmits the predetermined reciprocating rotary motion to the stirring part, and the holding member is detached from the stirring part.

11. A blood coagulation test method comprising:
a stirring step for stirring a test-object blood that is placed in a container by a stirring part;
a control step for transmitting a predetermined rotary motion to the stirring part and causing the stirring part to rotate in a reciprocating manner in a circumferential direction by rotating an elastic body in a reciprocating manner about an axis of the stirring part as a rotational axis and controlling the reciprocating rotation at a position separated by a predetermined diameter from the rotational axis, the elastic body being connected to the stirring part at a position separated by a predetermined diameter from an axis of the stirring part and capable of deforming in response to a force received through stirring of the test-object blood from the stirring part; and a measurement step for measuring a rotation angle pertaining to the reciprocating rotation of the stirring part.

* * * * *